(12) United States Patent
Cheng et al.

(10) Patent No.: US 12,048,643 B2
(45) Date of Patent: Jul. 30, 2024

(54) FLUID COLLECTION ASSEMBLIES INCLUDING AT LEAST ONE INFLATION DEVICE AND METHODS AND SYSTEMS OF USING THE SAME

(71) Applicant: PureWick Corporation, El Cajon, CA (US)

(72) Inventors: Jason Jishen Cheng, Rochester, NY (US); Eric Rehm, Greensboro, GA (US); Nicholas Austerman, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 138 days.

(21) Appl. No.: 17/326,980

(22) Filed: May 21, 2021

(65) Prior Publication Data

US 2021/0369495 A1 Dec. 2, 2021

Related U.S. Application Data

(60) Provisional application No. 63/030,685, filed on May 27, 2020.

(51) Int. Cl.
*A61F 5/451* (2006.01)
*A61F 5/44* (2006.01)
(Continued)

(52) U.S. Cl.
CPC ............ *A61F 5/451* (2013.01); *A61F 5/4405* (2013.01); *A61F 5/453* (2013.01); *A61F 5/455* (2013.01); *A61M 1/80* (2021.05)

(58) Field of Classification Search
CPC ........ A61F 5/451; A61F 5/4405; A61F 5/453; A61F 5/455; A61M 1/80
See application file for complete search history.

(56) References Cited

U.S. PATENT DOCUMENTS

| 1,032,841 A | 7/1912 | Koenig |
| 1,178,644 A | 4/1916 | Johnson |

(Continued)

FOREIGN PATENT DOCUMENTS

| AU | 2018216821 A1 | 8/2019 |
| CA | 2165286 C | 9/1999 |

(Continued)

OTHER PUBLICATIONS

US 9,908,683 B2, 03/2018, Sandhausen et al. (withdrawn)

(Continued)

*Primary Examiner* — Susan S Su
*Assistant Examiner* — Eric Rassavong
(74) *Attorney, Agent, or Firm* — Dorsey & Whitney LLP

(57) ABSTRACT

Embodiments disclosed herein are directed to fluid collection assemblies that include at least one inflation device, methods for using the same, and systems including the same. An example fluid collection assembly includes a fluid impermeable barrier defining at least one opening, a chamber, and at least one fluid outlet. The fluid collection assembly also includes at least one porous material disposed in the chamber. The fluid collection assembly further includes at least one inflation device. The inflation device includes at least one bladder having one or more walls defining an interior region. The inflation device also includes at least one valve configured to selectively permit flow of at least one inflation fluid into and out of the interior region to switch the at least one bladder between a first state and a second state.

13 Claims, 8 Drawing Sheets

(51) Int. Cl.
  *A61F 5/453* (2006.01)
  *A61F 5/455* (2006.01)
  *A61M 1/00* (2006.01)

(56) References Cited

U.S. PATENT DOCUMENTS

| | | |
|---|---|---|
| 1,742,080 A | 12/1929 | Jones |
| 1,979,899 A | 11/1934 | Obrien et al. |
| 2,262,772 A | 11/1941 | Peder |
| 2,326,881 A | 8/1943 | Packer |
| 2,379,346 A | 6/1945 | Farrell |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,699,815 A | 10/1972 | Holbrook |
| 3,726,277 A | 4/1973 | Hirschman |
| 3,742,952 A * | 7/1973 | Magers ............. A61M 1/684 604/133 |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,233,025 A | 11/1980 | Larson et al. |
| 4,233,978 A | 11/1980 | Hickey |
| 4,246,901 A | 1/1981 | Frosch et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,352,356 A | 10/1982 | Tong |
| 4,360,933 A | 11/1982 | Kimura et al. |
| 4,365,363 A | 12/1982 | Windauer |
| 4,387,726 A | 6/1983 | Denard |
| 4,425,130 A | 1/1984 | DesMarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | McNeil |
| 4,553,968 A | 11/1985 | Komis |
| 4,581,026 A | 4/1986 | Schneider |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,058,088 A | 10/1991 | Haas et al. |
| 5,071,347 A | 12/1991 | McGuire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |

(56) References Cited

U.S. PATENT DOCUMENTS

| | | |
|---|---|---|
| 5,195,997 A | 3/1993 | Carns |
| 5,203,699 A | 4/1993 | McGuire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | McDowall et al. |
| 5,752,944 A | 5/1998 | Dann et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,876,393 A | 3/1999 | Ahr et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork |
| 6,263,887 B1 | 7/2001 | Dunn |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,585,293 B2 | 9/2009 | Vermaak |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |

(56) References Cited

U.S. PATENT DOCUMENTS

| | | |
|---|---|---|
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,713,547 B2 | 7/2017 | Lee et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| D901,214 S | 11/2020 | Hu |
| 10,857,025 B2 | 12/2020 | Davis et al. |
| 10,865,017 B2 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,678 B2 | 4/2021 | Newton et al. |
| 10,974,874 B2 | 4/2021 | Ragias et al. |
| 11,000,401 B2 | 5/2021 | Ecklund et al. |

(56) References Cited

U.S. PATENT DOCUMENTS

| | | |
|---|---|---|
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,179,506 B2 | 11/2021 | Barr et al. |
| 11,226,376 B2 | 1/2022 | Yamauchi et al. |
| 11,369,508 B2 | 6/2022 | Ecklund et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,426,303 B2 | 8/2022 | Davis et al. |
| 11,529,252 B2 | 12/2022 | Glithero et al. |
| D1,010,109 S | 1/2024 | Ecklund et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | DiCamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |

(56) References Cited

U.S. PATENT DOCUMENTS

| | | |
|---|---|---|
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0005647 A1 | 1/2014 | Shuffler et al. |
| 2014/0031774 A1 | 1/2014 | Bengtson |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | McMenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-Schärli et al. |
| 2020/0129322 A1 | 4/2020 | Leuckel |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | McCourt |

(56) References Cited

U.S. PATENT DOCUMENTS

| | | |
|---|---|---|
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0267787 A1 | 9/2021 | Nazemi |
| 2021/0275343 A1 | 9/2021 | Sanchez et al. |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104981 A1 | 4/2022 | Jones |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0248836 A1 | 8/2022 | Cagle et al. |
| 2022/0257407 A1 | 8/2022 | Johannes et al. |
| 2022/0265462 A1 | 8/2022 | Alder et al. |
| 2022/0273482 A1 | 9/2022 | Johannes et al. |
| 2022/0280357 A1 | 9/2022 | Jagannathan et al. |
| 2022/0313222 A1 | 10/2022 | Austermann et al. |
| 2022/0313474 A1 | 10/2022 | Kriscovich et al. |
| 2022/0354685 A1 | 11/2022 | Davis et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0062944 A1 | 3/2023 | Vollenberg et al. |
| 2023/0062994 A1 | 3/2023 | Ecklund et al. |
| 2023/0089032 A1 | 3/2023 | Hughett et al. |
| 2023/0105001 A1 | 4/2023 | Whittome et al. |
| 2023/0138269 A1 | 5/2023 | Abdelal et al. |
| 2023/0145365 A1 | 5/2023 | Martin et al. |
| 2023/0277362 A1 | 9/2023 | Davis et al. |
| 2023/0404791 A1 | 12/2023 | Ecklund et al. |

FOREIGN PATENT DOCUMENTS

| | | | |
|---|---|---|---|
| CA | 2354132 A1 | 6/2000 | |
| CA | 2488867 C | 8/2007 | |
| CA | 3050918 A1 | 8/2018 | |
| CA | 3098571 A1 * | 11/2019 | ........... A61F 5/4401 |
| CA | 3098571 A1 | 11/2019 | |
| CN | 2269203 Y | 12/1997 | |
| CN | 1332620 A | 1/2002 | |
| CN | 1533755 A | 10/2004 | |
| CN | 1602825 A | 4/2005 | |
| CN | 1720888 A | 1/2006 | |
| CN | 2936204 Y | 8/2007 | |
| CN | 101262836 A | 9/2008 | |
| CN | 101522148 A | 9/2009 | |
| CN | 102159159 A | 8/2011 | |
| CN | 202184840 U | 4/2012 | |
| CN | 102481441 A | 5/2012 | |
| CN | 202463712 U | 10/2012 | |
| CN | 103533968 A | 1/2014 | |
| CN | 103717180 A | 4/2014 | |
| CN | 204562697 U | 8/2015 | |
| CN | 105411783 A | 3/2016 | |
| CN | 105451693 A | 3/2016 | |
| CN | 105534632 A | 5/2016 | |
| CN | 205849719 U | 1/2017 | |
| CN | 106726089 A | 5/2017 | |
| CN | 107847384 A | 3/2018 | |
| CN | 107920912 A | 4/2018 | |
| CN | 209285902 U | 8/2019 | |
| CN | 110381883 A | 10/2019 | |
| CN | 211198839 U | 8/2020 | |
| CN | 112566550 A | 3/2021 | |
| CN | 112603184 A | 4/2021 | |
| CN | 114007493 A | 2/2022 | |
| CN | 114375187 A | 4/2022 | |
| CN | 116096332 A | 5/2023 | |
| DE | 1516466 A1 | 6/1969 | |
| DE | 2721330 A1 | 11/1977 | |
| DE | 2742298 A1 | 3/1978 | |
| DE | 94075549 U1 | 5/1995 | |
| DE | 4443710 A1 | 6/1995 | |
| DE | 4416094 A1 | 11/1995 | |
| DE | 4236097 C2 | 10/1996 | |
| DE | 19619597 A1 | 11/1997 | |
| DE | 102005037762 B3 | 9/2006 | |
| DE | 102011103783 A1 | 12/2012 | |
| DE | 202015104597 U1 | 7/2016 | |
| DK | 9600118 | 11/1996 | |
| EP | 0032138 A2 | 7/1981 | |
| EP | 0066070 B1 | 12/1982 | |
| EP | 0274753 A2 | 7/1988 | |
| EP | 0119143 B1 | 11/1988 | |
| EP | 0483592 A1 | 5/1992 | |
| EP | 0610638 A1 | 8/1994 | |
| EP | 0613355 A1 | 9/1994 | |
| EP | 0613355 B1 | 1/1997 | |
| EP | 0787472 A1 | 8/1997 | |
| EP | 0966936 A1 | 12/1999 | |
| EP | 0987293 A1 | 3/2000 | |
| EP | 1063953 A1 | 1/2001 | |
| EP | 0653928 B1 | 10/2002 | |
| EP | 1332738 A1 | 8/2003 | |
| EP | 1382318 A1 | 1/2004 | |
| EP | 1089684 B1 | 10/2004 | |
| EP | 1616542 A1 | 1/2006 | |
| EP | 1382318 B1 | 5/2006 | |
| EP | 1063953 B1 | 1/2007 | |
| EP | 1872752 A1 | 1/2008 | |
| EP | 2180907 A1 | 5/2010 | |
| EP | 2380532 A1 | 10/2011 | |
| EP | 2389908 A1 | 11/2011 | |
| EP | 2601916 A1 | 6/2013 | |
| EP | 2676643 A1 | 12/2013 | |
| EP | 2997950 A2 | 3/2016 | |

(56) References Cited

FOREIGN PATENT DOCUMENTS

| | | |
|---|---|---|
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 4025163 A1 | 7/2022 |
| EP | 3463180 B1 | 3/2023 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |

(56) References Cited

FOREIGN PATENT DOCUMENTS

| | | | | |
|---|---|---|---|---|
| WO | 2011117292 A1 | 9/2011 | | |
| WO | 2011123219 A1 | 10/2011 | | |
| WO | 2011132043 A1 | 10/2011 | | |
| WO | 2012012908 A1 | 2/2012 | | |
| WO | 2012065274 A1 | 5/2012 | | |
| WO | 2012097462 A1 | 7/2012 | | |
| WO | 2012098796 A1 | 7/2012 | | |
| WO | 2012101288 A1 | 8/2012 | | |
| WO | 2012175916 A1 | 12/2012 | | |
| WO | 2013018435 A1 | 2/2013 | | |
| WO | 2013033429 A1 | 3/2013 | | |
| WO | 2013055434 A1 | 4/2013 | | |
| WO | WO-2013082397 A1 * | 6/2013 | ............... | A61F 5/44 |
| WO | 2013103291 A2 | 7/2013 | | |
| WO | 2013131109 A1 | 9/2013 | | |
| WO | 2013167478 A1 | 11/2013 | | |
| WO | 2013177716 A1 | 12/2013 | | |
| WO | 2014041534 A1 | 3/2014 | | |
| WO | 2014046420 A1 | 3/2014 | | |
| WO | 2014118518 A1 | 8/2014 | | |
| WO | 2014160852 A1 | 10/2014 | | |
| WO | 2015023599 A1 | 2/2015 | | |
| WO | 2015052348 A1 | 4/2015 | | |
| WO | 2015068384 A1 | 5/2015 | | |
| WO | 2015169403 A1 | 11/2015 | | |
| WO | 2015170307 A1 | 11/2015 | | |
| WO | 2015197462 A3 | 12/2015 | | |
| WO | 2016051385 A1 | 4/2016 | | |
| WO | 2016055989 A1 | 4/2016 | | |
| WO | 2016071894 A1 | 5/2016 | | |
| WO | 2016103242 A1 | 6/2016 | | |
| WO | 2016116915 A1 | 7/2016 | | |
| WO | 2016124203 A1 | 8/2016 | | |
| WO | 2016139448 A1 | 9/2016 | | |
| WO | 2016166562 A1 | 10/2016 | | |
| WO | 2016167535 A1 | 10/2016 | | |
| WO | 2016191574 A1 | 12/2016 | | |
| WO | 2016200088 A1 | 12/2016 | | |
| WO | 2016200361 A1 | 12/2016 | | |
| WO | 2016204731 A1 | 12/2016 | | |
| WO | WO-2017075226 A1 * | 5/2017 | ........... | A61F 5/0093 |
| WO | 2017152198 A1 | 9/2017 | | |
| WO | 2017153357 A1 | 9/2017 | | |
| WO | 2017162559 A1 | 9/2017 | | |
| WO | 2017205446 A1 | 11/2017 | | |
| WO | 2017209779 A1 | 12/2017 | | |
| WO | 2017210524 A1 | 12/2017 | | |
| WO | 2018022414 A1 | 2/2018 | | |
| WO | 2018044781 A1 | 3/2018 | | |
| WO | 2018056953 A1 | 3/2018 | | |
| WO | 2018090550 A1 | 5/2018 | | |
| WO | 2018138513 A1 | 8/2018 | | |
| WO | 2018144318 A1 | 8/2018 | | |
| WO | 2018144463 A1 | 8/2018 | | |
| WO | 2018150263 A1 | 8/2018 | | |
| WO | 2018150268 A1 | 8/2018 | | |
| WO | 2018152156 A1 | 8/2018 | | |
| WO | 2018183791 A1 | 10/2018 | | |
| WO | 2018150267 A3 | 11/2018 | | |
| WO | 2018235026 A1 | 12/2018 | | |
| WO | 2018235065 A1 | 12/2018 | | |
| WO | 2019004404 A1 | 1/2019 | | |
| WO | 2019065541 A1 | 4/2019 | | |
| WO | 2019096845 A1 | 5/2019 | | |
| WO | 2019150385 A1 | 8/2019 | | |
| WO | 2019161094 A1 | 8/2019 | | |
| WO | 2019188566 A1 | 10/2019 | | |
| WO | 2019190593 A1 | 10/2019 | | |
| WO | 2019212949 A1 | 11/2019 | | |
| WO | 2019212950 A1 | 11/2019 | | |
| WO | 2019212951 A1 | 11/2019 | | |
| WO | 2019212952 A1 | 11/2019 | | |
| WO | 2019212954 A1 | 11/2019 | | |
| WO | 2019212955 A1 | 11/2019 | | |
| WO | 2019212956 A1 | 11/2019 | | |
| WO | 2019214787 A1 | 11/2019 | | |
| WO | 2019214788 A1 | 11/2019 | | |
| WO | 2019226826 A1 | 11/2019 | | |
| WO | 2019239433 A1 | 12/2019 | | |
| WO | 2020000994 A1 | 1/2020 | | |
| WO | 2020020618 A1 | 1/2020 | | |
| WO | 2020038822 A1 | 2/2020 | | |
| WO | 2020088409 A1 | 5/2020 | | |
| WO | 2020049394 A3 | 6/2020 | | |
| WO | 2020120657 A1 | 6/2020 | | |
| WO | 2020152575 A1 | 7/2020 | | |
| WO | 2020182923 A1 | 9/2020 | | |
| WO | 2020204967 A1 | 10/2020 | | |
| WO | 2020209898 A1 | 10/2020 | | |
| WO | 2020242790 A1 | 12/2020 | | |
| WO | 2020251893 A1 | 12/2020 | | |
| WO | 2020256865 A1 | 12/2020 | | |
| WO | 2021007144 A1 | 1/2021 | | |
| WO | 2021007345 A1 | 1/2021 | | |
| WO | 2021010844 A1 | 1/2021 | | |
| WO | 2021016026 A1 | 1/2021 | | |
| WO | 2021016300 A1 | 1/2021 | | |
| WO | 2021025919 A1 | 2/2021 | | |
| WO | 2021034886 A1 | 2/2021 | | |
| WO | 2021041123 A1 | 3/2021 | | |
| WO | 2021086868 A1 | 5/2021 | | |
| WO | 2021094352 A1 | 5/2021 | | |
| WO | 2021094639 A1 | 5/2021 | | |
| WO | 2021102296 A1 | 5/2021 | | |
| WO | 2021138411 A1 | 7/2021 | | |
| WO | 2021138414 A1 | 7/2021 | | |
| WO | 2021155206 A1 | 8/2021 | | |
| WO | 2021173436 A1 | 9/2021 | | |
| WO | 2021195384 A1 | 9/2021 | | |
| WO | 2021207621 A1 | 10/2021 | | |
| WO | 2021211568 A1 | 10/2021 | | |
| WO | 2021216419 A1 | 10/2021 | | |
| WO | 2021216422 A1 | 10/2021 | | |
| WO | 2021231532 A1 | 11/2021 | | |
| WO | 2021247523 A1 | 12/2021 | | |
| WO | 2021257202 A1 | 12/2021 | | |
| WO | 2022006256 A1 | 1/2022 | | |
| WO | 2022031943 A1 | 2/2022 | | |
| WO | 2022035745 A1 | 2/2022 | | |
| WO | 2022076427 A2 | 4/2022 | | |
| WO | 2022086898 A1 | 4/2022 | | |
| WO | 2022098536 A1 | 5/2022 | | |
| WO | 2022125685 A1 | 6/2022 | | |
| WO | 2022140545 A1 | 6/2022 | | |
| WO | 2022150360 A1 | 7/2022 | | |
| WO | 2022150463 A1 | 7/2022 | | |
| WO | 2022159392 A1 | 7/2022 | | |
| WO | 2022170182 A1 | 8/2022 | | |
| WO | 2022182385 A1 | 9/2022 | | |
| WO | 2022192188 A1 | 9/2022 | | |
| WO | 2022192347 A1 | 9/2022 | | |
| WO | 2023014639 A1 | 2/2023 | | |
| WO | 2023014641 A1 | 2/2023 | | |
| WO | 2023034453 A1 | 3/2023 | | |
| WO | 2023038945 A1 | 3/2023 | | |
| WO | 2023038950 A1 | 3/2023 | | |
| WO | 2023049175 A1 | 3/2023 | | |
| WO | 2023086394 A1 | 5/2023 | | |
| WO | 2023191764 A1 | 10/2023 | | |

OTHER PUBLICATIONS

Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Corrected Notice of Allowability for U.S. Appl. No. 15/612,325 dated Mar. 17, 2021.

(56) References Cited

OTHER PUBLICATIONS

Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 14/952,591 dated Nov. 27, 2020.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.
Final Office Action for U.S. Appl. No. 16/899,956 dated Apr. 19, 2021.
Final Office Action for U.S. Appl. No. 16/904,868 dated Mar. 26, 2021.
Final Office Action for U.S. Appl. No. 16/905,400 dated Apr. 6, 2021.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
Issue Notification for U.S. Appl. No. 15/171,968 dated Mar. 3, 2021.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Issue Notification for U.S. Appl. No. 15/612,325 dated Mar. 24, 2021.
Non-Final Office Action for U.S. Appl. No. 14/592,591 dated Mar. 20, 2020.
Non-Final Office Action for U.S. Appl. No. 14/722,613 dated Jun. 13, 2019.
Non-Final Office Action for U.S. Appl. No. 14/947,759 dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/899,956 dated Oct. 16, 2020.
Non-Final Office Action for U.S. Appl. No. 16/904,868 dated Nov. 25, 2020.
Non-Final Office Action for U.S. Appl. No. 16/905,400 dated Dec. 2, 2020.
Non-Final Office Action for U.S. Appl. No. 17/088,272 dated Jan. 25, 2021.
Non-Final Office Action for U.S. Appl. No. 29/624,661 dated Apr. 28, 2021.
Non-Final Office Action for U.S. Appl. No. 29/624,661 dated Jul. 18, 2019.
Non-Final Office Action for U.S. Appl. No. 29/694,002 dated Jun. 24, 2020.
Notice of Allowance for U.S. Appl. No. 14/952,591 dated Apr. 5, 2021.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/221,106 dated May 1, 2019.
Notice of Allowance for U.S. Appl. No. 15/238,427 dated May 23, 2019.

(56) References Cited

OTHER PUBLICATIONS

Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Jan. 29, 2021.
Notice of Allowance for U.S. Appl. No. 29/694,002 dated Oct. 16, 2020.
Notice to File Missing Parts for U.S. Appl. No. 17/179,116 dated Mar. 3, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/146,946, filed Feb. 8, 2021.
U.S. Appl. No. 63/147,299, filed Feb. 9, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
Defendant and Counterclaim Plaintiff Sage Products, LLC's Answer, Defenses, and Counterclaims to Plaintiff's Amended Complaint, Nov. 1, 2019.
Memorandum Order, Feb. 2021, 14 pgs.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. No.'s 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Boehringer CareDry System—Second Generation for Non-Invasive Urinary Management for Females, Mar. 2021, 3 pgs.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-to-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.

(56) References Cited

OTHER PUBLICATIONS

"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", htttps://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Advisory Action for U.S. Appl. No. 16/245,726 dated Apr. 19, 2023.
Advisory Action for U.S. Appl. No. 16/369,676 dated Mar. 24, 2023.
Advisory Action for U.S. Appl. No. 16/433,773 dated Feb. 15, 2023.
Advisory Action for U.S. Appl. No. 16/452,258 dated Oct. 26, 2022.
Advisory Action for U.S. Appl. No. 16/478,180 dated Sep. 21, 2022.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/904,868 dated Jun. 15, 2022.
Advisory Action for U.S. Appl. No. 16/905,400 dated Feb. 16, 2022.
Advisory Action for U.S. Appl. No. 16/905,400 dated Jun. 9, 2021.
Advisory Action for U.S. Appl. No. 17/662,700 dated Jan. 30, 2023.
Corrected Notice of Allowability for U.S. Appl. No. 17/330,657 dated Dec. 9, 2021.
Final Office Action for U.S. Appl. No. 16/245,726 dated Nov. 25, 2022.
Final Office Action for U.S. Appl. No. 16/369,676 dated Dec. 5, 2022.
Final Office Action for U.S. Appl. No. 16/433,773 dated Oct. 25, 2022.
Final Office Action for U.S. Appl. No. 16/449,039 dated Aug. 1, 2022.
Final Office Action for U.S. Appl. No. 16/452,145 dated Mar. 25, 2022.
Final Office Action for U.S. Appl. No. 16/452,258 dated Jun. 14, 2022.
Final Office Action for U.S. Appl. No. 16/478,180 dated Jun. 22, 2022.
Final Office Action for U.S. Appl. No. 16/478,180 dated May 31, 2023.
Final Office Action for U.S. Appl. No. 16/904,868 dated Mar. 10, 2022.
Final Office Action for U.S. Appl. No. 16/905,400 dated Dec. 9, 2021.
Final Office Action for U.S. Appl. No. 17/051,399 dated Mar. 9, 2023.
Final Office Action for U.S. Appl. No. 17/051,550 dated May 23, 2023.
Final Office Action for U.S. Appl. No. 17/088,272 dated May 25, 2021.
Final Office Action for U.S. Appl. No. 17/444,792 dated Jun. 15, 2023.
Final Office Action for U.S. Appl. No. 17/451,345 dated May 3, 2023.
Final Office Action for U.S. Appl. No. 17/662,700 dated Sep. 30, 2022.
International Search Report and Written Opinion from International Application No. PCT/IB2021/057173 dated Nov. 5, 2021.
International Search Report and Written Opinion from International Application No. PCT/US2020/057562 dated Jan. 27, 2021.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
International Search Report and Written Opinion from International Application No. PCT/US2021/026607 dated Jul. 29, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
International Search Report and Written Opinion from International Application No. PCT/US2021/039866 dated Oct. 7, 2021.
International Search Report and Written Opinion from International Application No. PCT/US2021/043893 dated Nov. 22, 2021.

(56) References Cited

OTHER PUBLICATIONS

International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048211 dated Dec. 22, 2021.
International Search Report and Written Opinion from International Application No. PCT/US2021/048661 dated Feb. 14, 2022.
International Search Report and Written Opinion from International Application No. PCT/US2021/049404 dated Jan. 18, 2022.
International Search Report and Written Opinion from International Application No. PCT/US2021/051456 dated Jan. 19, 2022.
International Search Report and Written Opinion from International Application No. PCT/US2021/053593 dated Apr. 11, 2022.
International Search Report and Written Opinion from International Application No. PCT/US2021/055515 dated Jan. 28, 2022.
International Search Report and Written Opinion from International Application No. PCT/US2021/056566 dated Feb. 11, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.
International Search Report and Written Opinion from International Application No. PCT/US2022/011108 dated Apr. 22, 2022.
International Search Report and Written Opinion from International Application No. PCT/US2022/011281 dated Apr. 25, 2022.
International Search Report and Written Opinion from International Application No. PCT/US2022/011419 dated Jun. 7, 2022.
International Search Report and Written Opinion from International Application No. PCT/US2022/011421 dated Jun. 13, 2022.
International Search Report and Written Opinion from International Application No. PCT/US2022/012794 dated May 3, 2022.
International Search Report and Written Opinion from International Application No. PCT/US2022/014285 dated Sep. 28, 2022.
International Search Report and Written Opinion from International Application No. PCT/US2022/014749 dated Sep. 28, 2022.
International Search Report and Written Opinion from International Application No. PCT/US2022/015026 dated Oct. 31, 2022.
International Search Report and Written Opinion from International Application No. PCT/US2022/015045 dated Sep. 9, 2022.
International Search Report and Written Opinion from International Application No. PCT/US2022/015073 dated Sep. 8, 2022.
International Search Report and Written Opinion from International Application No. PCT/US2022/015418 dated Nov. 11, 2022.
International Search Report and Written Opinion from International Application No. PCT/US2022/015420 dated Nov. 18, 2022.
International Search Report and Written Opinion from International Application No. PCT/US2022/015471 dated May 16, 2022.
International Search Report and Written Opinion from International Application No. PCT/US2022/015492 dated Apr. 26, 2022.
International Search Report and Written Opinion from International Application No. PCT/US2022/015781 dated May 6, 2022.
International Search Report and Written Opinion from International Application No. PCT/US2022/016942 dated Jun. 8, 2022.
International Search Report and Written Opinion from International Application No. PCT/US2022/018159 dated Dec. 12, 2022.
International Search Report and Written Opinion from International Application No. PCT/US2022/018170 dated May 31, 2022.
International Search Report and Written Opinion from International Application No. PCT/US2022/019254 dated Jun. 7, 2022.
International Search Report and Written Opinion from International Application No. PCT/US2022/019480 dated Jun. 13, 2022.
International Search Report and Written Opinion from International Application No. PCT/US2022/021103 dated Jun. 23, 2022.
International Search Report and Written Opinion from International Application No. PCT/US2022/022111 dated Oct. 26, 2022.
International Search Report and Written Opinion from International Application No. PCT/US2022/023594 dated Jul. 12, 2022.
International Search Report and Written Opinion from International Application No. PCT/US2022/026667 dated Aug. 22, 2022.
International Search Report and Written Opinion from International Application No. PCT/US2022/030685 dated Oct. 31, 2022.
International Search Report and Written Opinion from International Application No. PCT/US2022/031032 dated Sep. 9, 2022.
International Search Report and Written Opinion from International Application No. PCT/US2022/032424 dated Oct. 11, 2022.
International Search Report and Written Opinion from International Application No. PCT/US2022/034457 dated Oct. 12, 2022.
International Search Report and Written Opinion from International Application No. PCT/US2022/034744 dated Dec. 9, 2022.
International Search Report and Written Opinion from International Application No. PCT/US2022/039018 dated Jan. 10, 2023.
International Search Report and Written Opinion from International Application No. PCT/US2022/039022 dated Jan. 10, 2023.
International Search Report and Written Opinion from International Application No. PCT/US2022/039711 dated Jan. 12, 2023.
International Search Report and Written Opinion from International Application No. PCT/US2022/039714 dated Nov. 22, 2022.
International Search Report and Written Opinion from International Application No. PCT/US2022/041085 dated Mar. 16, 2023.
International Search Report and Written Opinion from International Application No. PCT/US2022/041688 dated Nov. 21, 2022.
International Search Report and Written Opinion from International Application No. PCT/US2022/042719 dated Dec. 5, 2022.
International Search Report and Written Opinion from International Application No. PCT/US2022/042725 dated Dec. 19, 2022.
International Search Report and Written Opinion from International Application No. PCT/US2022/044107 dated Dec. 23, 2022.
International Search Report and Written Opinion from International Application No. PCT/US2022/044212 dated Jan. 20, 2023.
International Search Report and Written Opinion from International Application No. PCT/US2022/044243 dated Feb. 24, 2023.
Issue Notification for U.S. Appl. No. 14/952,591 dated Jul. 28, 2021.
Issue Notification for U.S. Appl. No. 16/899,956 dated Mar. 29, 2023.
Issue Notification for U.S. Appl. No. 16/905,400 dated Nov. 30, 2022.
Issue Notification for U.S. Appl. No. 17/088,272 dated Jun. 15, 2022.
Issue Notification for U.S. Appl. No. 17/330,657 dated Jun. 22, 2022.
Issue Notification for U.S. Appl. No. 29/624,661 dated Aug. 4, 2021.
Non-Final Office Action for U.S. Appl. No. 16/245,726 dated Jan. 21, 2022.
Non-Final Office Action for U.S. Appl. No. 16/369,676 dated Mar. 31, 2022.
Non-Final Office Action for U.S. Appl. No. 16/433,773 dated Apr. 11, 2023.
Non-Final Office Action for U.S. Appl. No. 16/433,773 dated Apr. 21, 2022.
Non-Final Office Action for U.S. Appl. No. 16/449,039 dated Apr. 27, 2023.
Non-Final Office Action for U.S. Appl. No. 16/449,039 dated Dec. 8, 2021.
Non-Final Office Action for U.S. Appl. No. 16/452,145 dated Mar. 28, 2023.
Non-Final Office Action for U.S. Appl. No. 16/452,145 dated Sep. 28, 2021.
Non-Final Office Action for U.S. Appl. No. 16/452,258 dated Apr. 26, 2023.
Non-Final Office Action for U.S. Appl. No. 16/452,258 dated Sep. 28, 2021.
Non-Final Office Action for U.S. Appl. No. 16/478,180 dated Dec. 20, 2022.
Non-Final Office Action for U.S. Appl. No. 16/478,180 dated Oct. 22, 2021.

(56) References Cited

OTHER PUBLICATIONS

Non-Final Office Action for U.S. Appl. No. 16/899,956 dated Sep. 2, 2021.
Non-Final Office Action for U.S. Appl. No. 16/904,868 dated Mar. 15, 2023.
Non-Final Office Action for U.S. Appl. No. 16/904,868 dated Oct. 5, 2021.
Non-Final Office Action for U.S. Appl. No. 16/905,400 dated Apr. 27, 2022.
Non-Final Office Action for U.S. Appl. No. 16/905,400 dated Jul. 22, 2021.
Non-Final Office Action for U.S. Appl. No. 17/051,550 dated Dec. 15, 2022.
Non-Final Office Action for U.S. Appl. No. 17/051,585 dated Mar. 29, 2023.
Non-Final Office Action for U.S. Appl. No. 17/179,116 dated Mar. 24, 2023.
Non-Final Office Action for U.S. Appl. No. 17/330,657 dated Aug. 11, 2021.
Non-Final Office Action for U.S. Appl. No. 17/444,792 dated Feb. 10, 2023.
Non-Final Office Action for U.S. Appl. No. 17/446,256 dated Apr. 13, 2023.
Non-Final Office Action for U.S. Appl. No. 17/448,811 dated Mar. 1, 2023.
Non-Final Office Action for U.S. Appl. No. 17/450,864 dated May 10, 2023.
Non-Final Office Action for U.S. Appl. No. 17/451,345 dated Dec. 7, 2022.
Non-Final Office Action for U.S. Appl. No. 17/451,354 dated May 3, 2023.
Non-Final Office Action for U.S. Appl. No. 17/453,260 dated Mar. 14, 2023.
Non-Final Office Action for U.S. Appl. No. 17/501,591 dated Apr. 25, 2023.
Non-Final Office Action for U.S. Appl. No. 17/653,137 dated Apr. 7, 2023.
Non-Final Office Action for U.S. Appl. No. 17/655,464 dated Mar. 14, 2023.
Non-Final Office Action for U.S. Appl. No. 17/662,700 dated Jul. 22, 2022.
Non-Final Office Action for U.S. Appl. No. 17/664,487 dated Jun. 8, 2023.
Non-Final Office Action for U.S. Appl. No. 29/741,751 dated Jan. 18, 2022.
Notice of Allowance for U.S. Appl. No. 14/952,591 dated Jul. 8, 2021.
Notice of Allowance for U.S. Appl. No. 16/449,039 dated Dec. 15, 2022.
Notice of Allowance for U.S. Appl. No. 16/899,956 dated Apr. 19, 2022.
Notice of Allowance for U.S. Appl. No. 16/899,956 dated Aug. 10, 2022.
Notice of Allowance for U.S. Appl. No. 16/899,956 dated Dec. 1, 2022.
Notice of Allowance for U.S. Appl. No. 16/899,956 dated Dec. 29, 2021.
Notice of Allowance for U.S. Appl. No. 16/905,400 dated Aug. 17, 2022.
Notice of Allowance for U.S. Appl. No. 17/088,272 dated Aug. 5, 2021.
Notice of Allowance for U.S. Appl. No. 17/088,272 dated Mar. 4, 2022.
Notice of Allowance for U.S. Appl. No. 17/088,272 dated Nov. 24, 2021.
Notice of Allowance for U.S. Appl. No. 17/330,657 dated Mar. 16, 2022.
Notice of Allowance for U.S. Appl. No. 17/330,657 dated Nov. 26, 2021.
Notice of Allowance for U.S. Appl. No. 17/461,036 dated Feb. 22, 2023.
Notice of Allowance for U.S. Appl. No. 17/461,036 dated Oct. 6, 2022.
Notice of Allowance for U.S. Appl. No. 17/662,700 dated Mar. 28, 2023.
Notice of Allowance for U.S. Appl. No. 17/663,046 dated Jan. 30, 2023.
Notice of Allowance for U.S. Appl. No. 29/624,661 dated Apr. 28, 2021.
Notice of Allowance for U.S. Appl. No. 29/694,002 dated Apr. 29, 2021.
Notice of Allowance for U.S. Appl. No. 29/741,751 dated Jun. 9, 2022.
Restriction Requirement for U.S. Appl. No. 16/433,773 dated Dec. 7, 2021.
Restriction Requirement for U.S. Appl. No. 16/478,180 dated May 25, 2021.
Restriction Requirement for U.S. Appl. No. 17/446,256 dated Jan. 23, 2023.
Restriction Requirement for U.S. Appl. No. 17/646,771 dated Apr. 6, 2023.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036, filed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.

(56) References Cited

OTHER PUBLICATIONS

U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/047,374, filed Jul. 2, 2020.
U.S. Appl. No. 63/067,542, filed Aug. 19, 2020.
U.S. Appl. No. 63/073,545, filed Sep. 2, 2020.
U.S. Appl. No. 63/073,553, filed Sep. 2, 2020.
U.S. Appl. No. 63/094,646, filed Oct. 21, 2020.
U.S. Appl. No. 63/109,084, filed Nov. 3, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/147,013, filed Feb. 8, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Application No. 63/308, 190 filed Feb. 9, 2022.
*PureWick Corporation* v. *Sage Products, LLC* Transcripts vol. 5, Apr. 1, 2022, 72 pages.
*PureWick Corporation* v. *Sage Products, LLC* Transcripts vol. 1, Mar. 28, 2022, 99 pages.
*PureWick Corporation* v. *Sage Products, LLC* Transcripts vol. 2, Mar. 29, 2022, 106 pages.
*PureWick Corporation* v. *Sage Products, LLC* Transcripts vol. 3, Mar. 30, 2022, 115 pages.
*PureWick Corporation* v. *Sage Products, LLC* Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.

(56) References Cited

OTHER PUBLICATIONS

Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
Tsipenyuk, et al., "Use of biomimetic hexagonal surface texture in friction against lubricated skin", Journal of The Royal Society—Interface, 2014, pp. 1-6.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021, 3 pages.
Advisory Action for U.S. Appl. No. 16/478,180 dated Sep. 7, 2023.
Advisory Action for U.S. Appl. No. 17/051,550 dated Sep. 8, 2023.
Advisory Action for U.S. Appl. No. 17/444,792 dated Aug. 25, 2023.
Final Office Action for U.S. Appl. No. 16/369,676 dated Aug. 31, 2023.
Final Office Action for U.S. Appl. No. 17/051,585 dated Jul. 27, 2023.
Final Office Action for U.S. Appl. No. 17/446,256 dated Sep. 19, 2023.
Final Office Action for U.S. Appl. No. 17/448,811 dated Aug. 3, 2023.
Final Office Action for U.S. Appl. No. 17/453,260 dated Oct. 5, 2023.
Final Office Action for U.S. Appl. No. 17/653,137 dated Sep. 21, 2023.
Final Office Action for U.S. Appl. No. 17/655,464 mailed Sep. 1, 2023.
International Search Report and Written Opinion from International Application No. PCT/US2022/043818 dated Mar. 24, 2023.
International Search Report and Written Opinion from International Application No. PCT/US2022/044208 dated May 8, 2023.
International Search Report and Written Opinion from International Application No. PCT/US2022/049300 dated Jun. 6, 2023.
International Search Report and Written Opinion from International Application No. PCT/US2022/050909 dated Jul. 24, 2023.
International Search Report and Written Opinion from International Application No. PCT/US2023/012696 dated Jul. 6, 2023.
Non-Final Office Action for U.S. Appl. No. 17/051,399 dated Aug. 18, 2023.
Non-Final Office Action for U.S. Appl. No. 17/446,654 dated Sep. 8, 2023.
Non-Final Office Action for U.S. Appl. No. 17/646,771 dated Jul. 5, 2023.
Non-Final Office Action for U.S. Appl. No. 17/657,474 dated Sep. 12, 2023.
Non-Final Office Action for U.S. Appl. No. 17/661,090 dated Jul. 6, 2023.
Non-Final Office Action for U.S. Appl. No. 17/663,330 dated Jun. 29, 2023.
Non-Final Office Action for U.S. Appl. No. 18/139,523 dated Aug. 17, 2023.
Non-Final Office Action for U.S. Appl. No. 18/140,751 dated Sep. 14, 2023.
Notice of Allowance for U.S. Appl. No. 16/245,726 dated Jul. 6, 2023.
Notice of Allowance for U.S. Appl. No. 17/051,554 dated Jul. 6, 2023.
Notice of Allowance for U.S. Appl. No. 17/461,036 dated Jun. 30, 2023.
Notice of Allowance for U.S. Appl. No. 17/662,700 dated Jul. 28, 2023.
Notice of Allowance for U.S. Appl. No. 18/299,788 dated Jul. 24, 2023.
Restriction Requirement for U.S. Appl. No. 17/051,600 dated Sep. 21, 2023.
Restriction Requirement for U.S. Appl. No. 17/645,821 dated Jul. 12, 2023.
Restriction Requirement for U.S. Appl. No. 17/657,474 dated Jun. 30, 2023.
U.S. Appl. No. 15/611,587, filed Jun. 1, 2017.
U.S. Appl. No. 15/612,325, filed Jun. 2, 2017.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 63/150,640, filed Feb. 18, 2021.
Merriam-Webster Dictionary, , "Embed Definition & Meaning", https://www.merriam-webster.com/dictionary/embed last accessed Aug. 3, 2023, 2003.
Advisory Action for U.S. Appl. No. 16/433,773 dated Dec. 29, 2023.
Advisory Action for U.S. Appl. No. 16/904,868 dated Jan. 2, 2024.
Advisory Action for U.S. Appl. No. 17/051,585 dated Oct. 17, 2023.
Advisory Action for U.S. Appl. No. 17/179,116 dated Jan. 8, 2024.
Advisory Action for U.S. Appl. No. 17/446,256 dated Dec. 8, 2023.
Advisory Action for U.S. Appl. No. 17/448,811 dated Nov. 15, 2023.
Advisory Action for U.S. Appl. No. 17/451,345 dated Oct. 20, 2023.
Advisory Action for U.S. Appl. No. 17/453,260 dated Dec. 22, 2023.
Advisory Action for U.S. Appl. No. 17/653,137 dated Dec. 1, 2023.
Advisory Action for U.S. Appl. No. 17/655,464 dated Dec. 13, 2023.
Communication of Notice of Opposition of European Application No. 17807547.9 dated Jan. 5, 2024.
Corrected Notice of Allowability for U.S. Appl. No. 16/369,676 dated Dec. 7, 2023.
Final Office Action for U.S. Appl. No. 16/433,773 dated Oct. 10, 2023.
Final Office Action for U.S. Appl. No. 16/449,039 dated Nov. 21, 2023.
Final Office Action for U.S. Appl. No. 16/452,258 dated Dec. 21, 2023.
Final Office Action for U.S. Appl. No. 16/904,868 dated Nov. 2, 2023.
Final Office Action for U.S. Appl. No. 17/051,399 dated Jan. 8, 2024.
Final Office Action for U.S. Appl. No. 17/179,116 dated Oct. 31, 2023.
Final Office Action for U.S. Appl. No. 17/450,864 dated Dec. 28, 2023.
Final Office Action for U.S. Appl. No. 17/451,354 dated Oct. 30, 2023.
Final Office Action for U.S. Appl. No. 17/501,591 dated Nov. 14, 2023.
Final Office Action for U.S. Appl. No. 17/646,771 dated Dec. 21, 2023.

(56) References Cited

OTHER PUBLICATIONS

Final Office Action for U.S. Appl. No. 17/661,090 dated Dec. 11, 2023.
Final Office Action for U.S. Appl. No. 17/663,330 dated Dec. 12, 2023.
Final Office Action for U.S. Appl. No. 17/664,487 dated Jan. 4, 2024.
Final Office Action for U.S. Appl. No. 18/139,523 dated Dec. 22, 2023.
Final Office Action for U.S. Appl. No. 18/164,800 dated Dec. 6, 2023.
International Search Report and Written Opinion from International Application No. PCT/US2023/018474 dated Sep. 11, 2023.
International Search Report and Written Opinion from International Application No. PCT/US2023/024805 dated Dec. 14, 2023.
Issue Notification for U.S. Appl. No. 16/245,726 dated Oct. 18, 2023.
Issue Notification for U.S. Appl. No. 17/461,036 dated Oct. 11, 2023.
Issue Notification for U.S. Appl. No. 17/663,046 dated Dec. 20, 2023.
Non-Final Office Action for U.S. Appl. No. 16/452,145 dated Nov. 2, 2023.
Non-Final Office Action for U.S. Appl. No. 16/478,180 dated Nov. 7, 2023.
Non-Final Office Action for U.S. Appl. No. 17/051,550 dated Oct. 24, 2023.
Non-Final Office Action for U.S. Appl. No. 17/051,585 dated Jan. 8, 2024.
Non-Final Office Action for U.S. Appl. No. 17/444,792 dated Nov. 17, 2023.
Non-Final Office Action for U.S. Appl. No. 17/453,560 dated Oct. 16, 2023.
Non-Final Office Action for U.S. Appl. No. 17/645,821 dated Oct. 25, 2023.
Non-Final Office Action for U.S. Appl. No. 17/653,137 dated Jan. 18, 2024.
Non-Final Office Action for U.S. Appl. No. 17/808,354 dated Nov. 28, 2023.
Non-Final Office Action for U.S. Appl. No. 18/140,163 dated Nov. 9, 2023.
Non-Final Office Action.for U.S. Appl. No. 18/198,464 dated Dec. 7, 2023.
Notice of Allowance for U.S. Appl. No. 16/369,676 dated Nov. 14, 2023.
Notice of Allowance for U.S. Appl. No. 17/051,554 dated Oct. 18, 2023.
Notice of Allowance for U.S. Appl. No. 17/662,700 dated Nov. 15, 2023.
Notice of Allowance for U.S. Appl. No. 18/299,788 dated Nov. 6, 2023.
Restriction Requirement for U.S. Appl. No. 18/134,857 dated Oct. 23, 2023.
Submission in Opposition Proceedings for European Application No. 17807547.9 filed Jan. 10, 2024.
U.S. Appl. No. 17/451,719, filed Oct. 19, 2021.
U.S. Appl. No. 18/389,009, filed Nov. 13, 2023.
U.S. Appl. No. 18/415,080, filed Jan. 17, 2024.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 63/596,012, filed Nov. 3, 2023.
U.S. Appl. No. 63/608,553, filed Dec. 11, 2023.
Wikipedia Article, "Zylinder (Geometrie)", https://de.wikipedia.org/w/index.php?title=Zylinder (Geometrie)&oldid=154862081, version of Jun. 1, 2016, 7 pages.
Advisory Action for U.S. Appl. No. 16/449,039 mailed Jan. 25, 2024.
Advisory Action for U.S. Appl. No. 17/451,354 mailed Jan. 30, 2024.
Advisory Action for U.S. Appl. No. 18/164,800 mailed Feb. 12, 2024.
Final Office Action for U.S. Appl. No. 17/446,654 mailed Jan. 31, 2024.
Final Office Action for U.S. Appl. No. 18/140,751 mailed Jan. 17, 2024.
Non-Final Office Action for U.S. Appl. No. 17/051,600 mailed Jan. 17, 2024.
Non-Final Office Action for U.S. Appl. No. 17/446,256 mailed Feb. 13, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/664,914 mailed Jan. 31, 2024.
Non-Final Office Action for U.S. Appl. No. 18/134,857 mailed Jan. 25, 2024.
Notice of Allowance for U.S. Appl. No. 17/051,550 mailed Feb. 7, 2024.
Notice of Allowance for U.S. Appl. No. 17/453,560 mailed Jan. 31, 2024.
Supplemental Notice of Allowance for U.S. Appl. No. 17/051,554 mailed Feb. 14, 2024.
U.S. Appl. No. 18/294,370, filed Feb. 1, 2024.
U.S. Appl. No. 18/294,403, filed Feb. 1, 2024.
U.S. Appl. No. 18/426,795, filed Jan. 30, 2024.
U.S. Appl. No. 18/681,987, filed Feb. 7, 2024.
U.S. Appl. No. 18/682,006, filed Feb. 7, 2024.

* cited by examiner

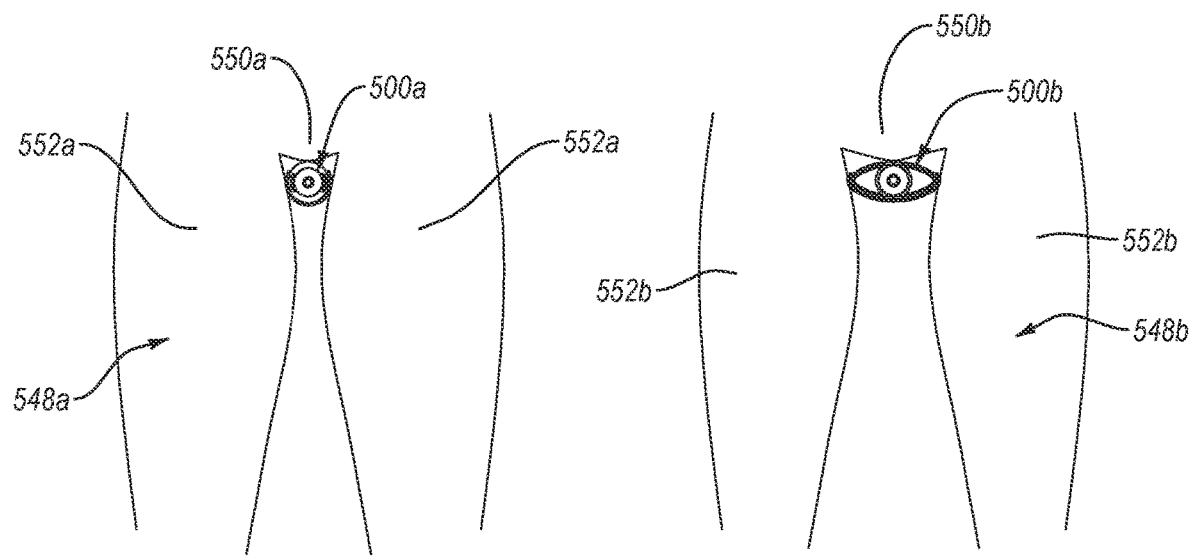

FLUID COLLECTION ASSEMBLIES INCLUDING AT LEAST ONE INFLATION DEVICE AND METHODS AND SYSTEMS OF USING THE SAME

BACKGROUND

A person or animal may have limited or impaired mobility so typical urination processes are challenging or impossible. For example, a person may experience or have a disability that impairs mobility. A person may have restricted travel conditions such as those experienced by pilots, drivers, and workers in hazardous areas. Additionally, sometimes bodily fluids collection is needed for monitoring purposes or clinical testing.

Urinary catheters, such as a Foley catheter, can address some of these circumstances, such as incontinence. Unfortunately, urinary catheters can be uncomfortable, painful, and can lead to complications, such as infections. Additionally, bed pans, which are receptacles used for the toileting of bedridden patients are sometimes used. However, bedpans can be prone to discomfort, spills, and other hygiene issues.

SUMMARY

Embodiments disclosed herein are directed to fluid collection assemblies that include at least one inflation device, methods for using the same, and systems including the same. In an embodiment, a fluid collection assembly is disclosed. The fluid collection assembly includes a fluid impermeable barrier defining a chamber, at least one opening, and at least one fluid outlet. The fluid collection assembly also includes at least one porous material disposed in the chamber. The fluid collection assembly further includes at least one inflation device including at least one bladder and at least one valve. The at least one bladder includes one or more walls defining an interior region. The at least one valve is configured to selectively permit at least one inflation fluid to flow into and out of the interior region to switch the at least one bladder between a first state and a second state. An amount of the at least one inflation fluid present in the interior region is greater when the at least one bladder is in the second state than when the at least one bladder is in the first state.

In an embodiment, a system is disclosed. The system includes a fluid collection assembly, a fluid storage container, a vacuum source, and one or more conduits. The one or more conduits operably couple at least one fluid outlet of the fluid collection assembly, the fluid storage container, and the vacuum source together. The fluid collection assembly of the system includes any one of the fluid collection assemblies disclosed herein.

In an embodiment, a method of using a fluid collection assembly is disclosed. The method includes positioning at least one opening of the fluid collection assembly adjacent to a female urethra or to receive a male penis therethrough. The fluid collection assembly includes a fluid impermeable barrier defining the at least one opening, a chamber, and the at least one fluid outlet. The fluid collection assembly also includes at least one porous material disposed in the chamber. The fluid collection assembly further includes at least one inflation device including at least one bladder and at least one valve, the at least one bladder including one or more walls defining an interior region. The method includes flowing at least one inflation fluid through the at least one valve and into the interior region of the at least one inflation element.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 5A is a schematic illustration of a first fluid collection assembly being used with a first female patient, according to an embodiment.

FIG. 5B is a schematic illustrated of a second fluid collection assembly being used with a second female patient, according to an embodiment.

DETAILED DESCRIPTION

Figure 1A:
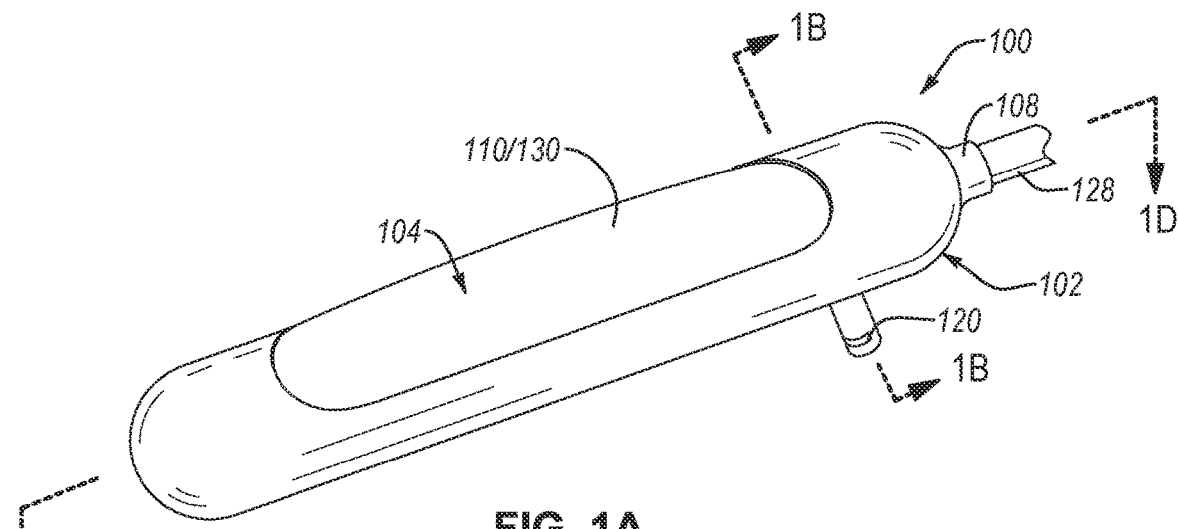
FIG. 1A is an isometric view of a fluid collection assembly configured to be used to collect bodily fluids from a female urethral opening, according to an embodiment.

Embodiments disclosed herein are directed to fluid collection assemblies that include at least one inflation device, methods for using the same, and systems including the same. An example fluid collection assembly includes a fluid impermeable barrier defining at least one opening, a chamber, and at least one fluid outlet. The fluid collection assembly also includes at least one porous material disposed in the chamber. As previously discussed, the fluid collection assembly further includes at least one inflation device. The inflation device includes at least one bladder having one or more walls defining an interior region. The inflation device also includes at least one valve configured to selectively permit fluid flow into and out of the interior region to switch the at least one bladder between a first state (e.g., a deflated and/or initial state) and a second state (e.g., an at least partially inflated state). The inflation device may facilitate securement of the fluid collection assembly with certain patients (e.g., underweight patients or patients with thin thighs) when the bladder of the inflation device is in the second state.

The fluid collection assembly is configured to be positioned about or around the pubic region of a patient. When the patient is a female, the pubic region may include the vulva (e.g., labia majora, labia minora, clitoris, urethral opening, etc.), mons pubis, the perineum, buttocks, and the inner thighs of the patient. When the patient is a male, the pubic region may include the penis, the testicles, the mons pubis, the buttocks, and the inner thighs of the patient.

The fluid collection assembly may be flexible thereby allowing the fluid collection assembly to conform to the size and topography of the pubic region since the size and topography of the pubic region may vary significantly from person to person. Conforming the fluid collection assembly to the pubic region may prevent or inhibit embarrassing and unsanitary leaks of bodily fluids (e.g., urine, blood, sweat, etc.). In some embodiments, the fluid collection assembly may rely on contact pressure from the thighs of the individual to remain conformed to the pubic region. However, it has been found that the thighs of some individuals may not provide sufficient contact pressure to allow the fluid collection assembly to remain conformed to the pubic when the fluid collection assembly is in the first (e.g., deflated) state. For instance, it has been found that underweight patients and other patients having thin thighs may not provide sufficient contact pressure to the fluid collection assembly to allow the fluid collection assembly to remain conformed to the pubic region when the fluid collection assembly is in the first state. Some conventional fluid collection assemblies that do not include the inflation device may have similar problems remaining conformed to the pubic region.

The inflatable devices disclosed herein allow the fluid collection assemblies disclosed herein to remain conformed to the pubic region even when the patient is underweight or has thin thighs. For example, when the fluid collection assembly does not have sufficient contact pressure from the thighs to remain conformed to the pubic region, at least one inflation fluid (e.g., gas or liquid) may be added to the interior region of the bladder through the valve. Adding the fluid to the interior region switches the bladder from the first state to the second state. Changing the bladder from the first state to the second shape also changes the shape and/or size of the fluid collection assembly. The changes in the shape and/or size of the fluid collection assembly may allow the fluid collection assembly to press against the thighs so the thighs provide sufficient contact pressure to allow the fluid collection assembly to remain conformed to the female anatomy.

The fluid collection assembly is configured to be disposed against the patient so the opening of the fluid impermeable barrier is disposed adjacent to at least the urethral opening of the patient. After positioning the fluid collection assembly, the patient may discharge bodily fluids, either controllably or uncontrollably. The porous material may remove the bodily fluids from the patient and move the bodily fluids through the opening and the chamber to the fluid outlet. The bodily fluids may be removed from the chamber via the fluid outlet by using at least one gravity (e.g., the fluid outlet is at the gravimetric low point of the chamber) or a suction force provided by a vacuum which suctions the bodily fluids from the chamber.

Figure 1B:
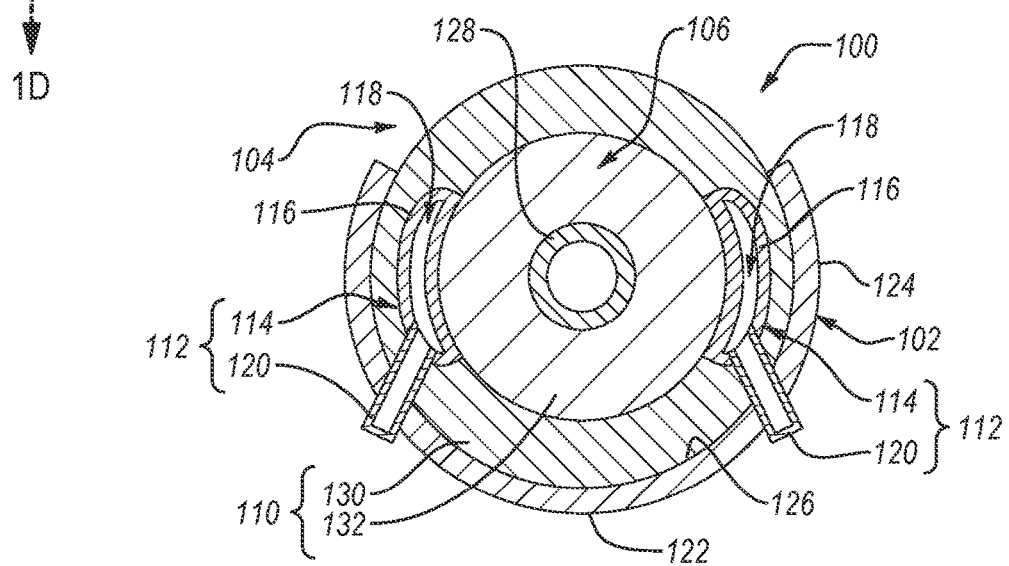
FIGS. 1B and 1C are schematic cross-sectional views of the fluid collection assembly taken along plane 1B-1B when a bladder of the fluid collection assembly is in a first state and in a second state, respectively, according to an embodiment.
Figure 1C:
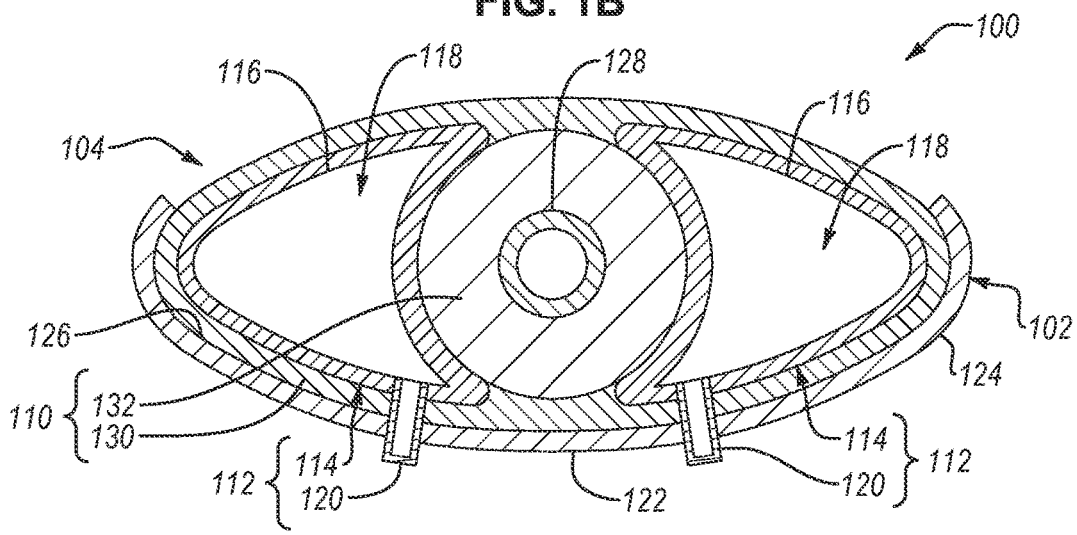
Figure 1D:
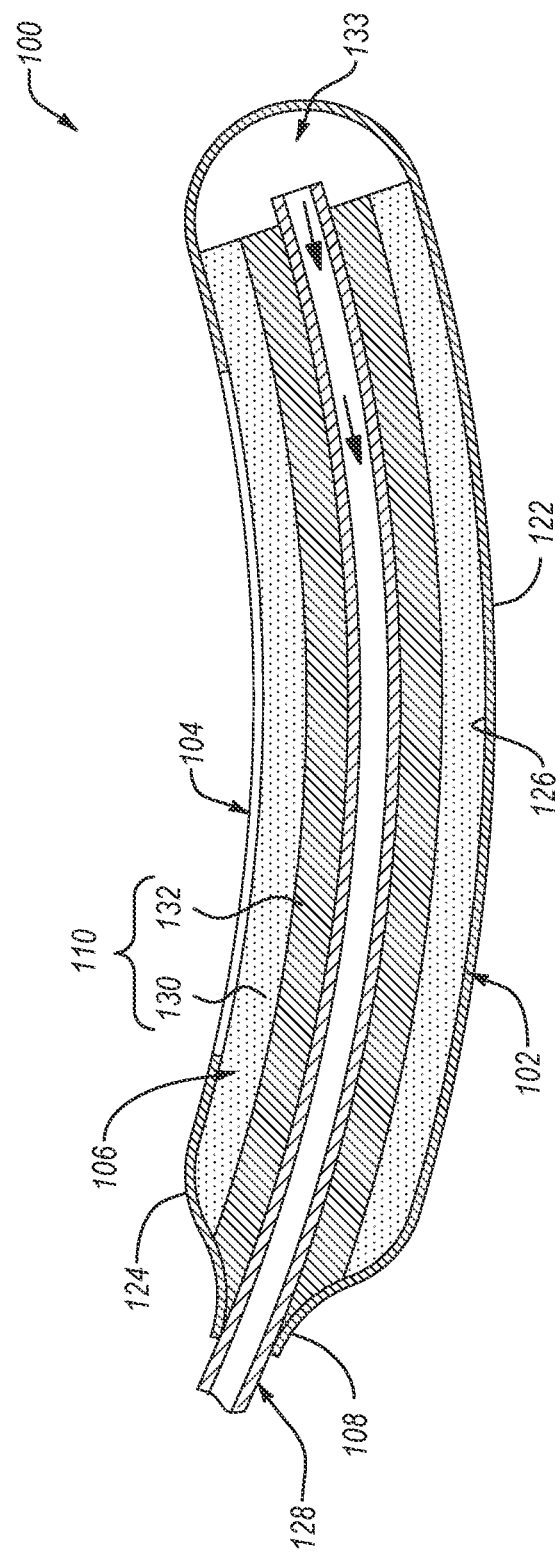
FIG. 1D is a schematic cross-sectional view of the fluid collection assembly taken along plane 1D-1D, according to an embodiment.

FIG. 1A is an isometric view of a fluid collection assembly 100 configured to be used to collect bodily fluids from a female urethral opening, according to an embodiment. FIGS. 1B and 1C are schematic cross-sectional views of the fluid collection assembly 100 taken along plane 1B-1B when a bladder 114 of the fluid collection assembly 100 is in a first state and in a second state, respectively, according to an embodiment. FIG. 1D is a schematic cross-sectional view of the fluid collection assembly 100 taken along plane 1D-1D, according to an embodiment. The fluid collection assembly 100 includes a fluid impermeable barrier 102 defining at least one opening 104, a chamber 106, and at least one fluid outlet 108. The fluid collection assembly 100 also includes at least one porous material 110 disposed chamber 106. The fluid collection assembly 100 further includes at least one inflation device 112 configured to change the shape and/or size of the fluid collection assembly 100.

The inflation device 112 includes a bladder 114. The bladder 114 includes one or more walls 116 defining an interior region 118. The inflation device 112 also includes at least one valve 120 in fluid communication with the interior region 118. The valve 120 is configured to selectively permit flow of an inflation fluid into and/or out the interior region 118. For example, the valve 120 may allow an inflation fluid to enter the interior region 118 when it is desirable to at least one of increase the size or change the shape of the bladder 114 which, in turn, at least one of increases the size or changes the shape of the fluid collection assembly 100. The valve 120 may also enable removing the inflation fluid from the interior region 118 when it is desirable to at least one of decrease the size or change the shape (e.g., return to the initial shape) of the bladder 114 which, in turn, at least one of decreases the size or changes the shape of the fluid collection assembly 100.

Disposing or removing the inflation fluids into and from the inflation region 118 changes the state of the bladder 114. The bladder 114 may exhibit at least a first state and a second state. The amount (volume or weight) of inflation fluids present in the inflation region 118 is greater when the bladder 114 is in the second state than when the bladder 114 is in the first state. In an example, as shown in FIG. 1B, the bladder 114 is in the first state when the bladder 114 is in a deflated state (e.g., there are no or substantially no fluids in the inflation region 118). However, it is noted that the bladder 114 may be in the first state when some inflation fluids are present in the inflation region 118. The bladder 114 generally also correspond to an initial state of the bladder 114 (i.e., generally, the bladder 114 is not provided with inflation fluids) though, in some examples, the first state of the bladder 114 may not correspond to the initial state of the bladder 114 (e.g., the bladder 114 is provided with fluids). In an example, as shown in FIG. 1C, the bladder 114 is in the first state when the bladder 114 is in an at least partially inflated state. The bladder 114 is generally not in the initial state when the bladder 114 is in the second state though, in some examples, the initial state and the second state of the bladder 114 are the same (e.g., when the bladder 114 is provided with fluids).

The bladder 114 may exhibit one or more additional states (e.g., third state, fourth state, and so forth) besides the first and second states discussed above. In an embodiment, the one or more additional states may include less inflation fluids in the inflation region 118 (e.g., is more deflated) than the first state (e.g., the first state is a partially inflated state). In such an embodiment, the one or more additional states may include a deflated or partially deflated state and may be formed by removing inflation fluids from the inflation region 118 when the bladder 114 is in the first or second state. In an embodiment, the one or more additional states may include more inflation fluids in the inflation region 118 (e.g., is more inflated) than the first state (e.g., the first state is a deflated or partially inflated state) and include less inflation fluids in the inflation region 118 than the second state. In such an embodiment, the one or more additional states include a partially inflated state and may be formed by adding or removing inflation fluids to the inflation region 118 when the bladder 114 is in the first state or second state, respectively. In an embodiment, the one or more additional states may include more inflation fluids in the inflation region 118 than the second state (e.g., the second state is a partially inflated state). In such an embodiment, the one or more additional states may be an at least partially inflated state and may be formed by adding inflation fluids to the inflation region 118 when the bladder 114 is in the first state or second state. It is noted that, in some embodiments, the bladder 114 may only include the first and second states.

As shown in FIGS. 1B and 1C, switching the bladder 114 from the first state to the second state (or any of the other states thereof) changes the shape and/or size of the fluid collection assembly 100 and the bladder 114. For example, referring to FIG. 1B, the fluid collection assembly 100 may exhibit a generally circular cross-sectional shape (e.g., the fluid collection assembly 100 exhibits a generally cylindrical shape, as shown in FIG. 1A) when the bladder 114 is in the first state. The bladder 114 may also exhibit a thin generally crescent cross-sectional shape when the bladder 114 is in the first state. It is noted that the fluid collection assembly 100 and/or the bladder 114 may exhibit different shapes when the bladder 114 is in the first state than the shapes illustrated in FIG. 1B. Switching the bladder 114 to the second state changes the shape of the fluid collection assembly 100, as shown in FIG. 1C, to a generally oblong cross-sectional shape and the bladder 114 into a wide generally crescent shape (i.e., a generally triangular shape). Further, switching the bladder 114 from the first state to the second state increases the size of the fluid collection assembly 100 and the bladder 114. For example, the increased size of the fluid collection assembly 100 may allow the fluid collection assembly 100 to contact and press against the inner thighs of a patient, even an underweight patient or a patient with thin thighs, allowing the fluid collection assembly 100 to remain conformed to the pubic region of the patient. It is noted that inflation fluids may be removed from the inflation region 118 using the valve 120, for example, when too much inflation fluids are added to the inflation region 118 which may at least one of increase the risk that the bladder 114 ruptures, make the fluid collection assembly 100 more uncomfortable, or increase the likelihood that the fluid collection assembly 100 leaks bodily fluids.

The walls 116 are formed from a material is substantially impermeable to the inflation fluid (e.g., substantially impermeable to a gas and/or a liquid) which allows the bladder 114 to retain the inflation fluids without embarrassing leaks. The walls 116 may also be formed from a flexible material. The flexible material of the walls 116 allows the bladder 114 and, by extension, the fluid collection assembly 100 to at least one of increase in size or change a shape thereof. For example, the flexible material of the walls 116 allow the interior region 118 to increase a volume thereof when the interior region 118 receives an inflation fluid and decrease a volume thereof when inflation fluids are removed from the interior region 118. Examples of materials that may form the walls 116 of the bladder 114 include silicone, rubber, latex, polychloroprene, nylon fabric, polypropylene, polyvinyl chloride, nitrile rubber, other suitable polymers, a metal foil, a composite, or combinations thereof. It is noted that the walls 116 do not contact the patient in the illustrated embodiment and might be formed from a biocompatible material. In an embodiment, the walls 116 are configured to stretch (e.g., elastically or plastically stretch) so the walls 116 remain taut when the bladder 114 is at least partially inflated. In an embodiment, the wall 116 forms a plurality of wrinkles when the bladder 114 is at least partially deflated and adding inflation fluid into the inflation region 118 decreases the wrinkles, similar to an accordion.

The valve 120 may include any suitable valve configured to allow for the controllable addition and remove of inflation fluids from the inflation region 118. In an embodiment, the valve 120 is a luer valve and includes a male-tapper fitting or a female-taper fitting. In an embodiment, the valve 120 includes a fluid impermeable membrane with a slit or opening formed. The slit or opening of the fluid impermeable membrane remains substantially closed when no external load is applied thereto but opens when an external load is applied thereto (e.g., an external load caused by pressing a syringe against the fluid impermeable membrane). In an embodiment, the valve 120 may include a mechanical valve, such as a ball valve, a butterfly valve, or any other suitable mechanical valve. The mechanical valve may be manually operated or controlled using a computer. In an embodiment, the valve 120 may include a check valve to limit leaks from the bladder 114 and to make the fluid collection assembly 100 easier to use. In such an embodiment, the valve 120 may only add or remove (but not both) inflation fluid from the inflation region 118 and, as such, the fluid collection assembly 100 is configured for single use.

In an embodiment, as illustrated, the valve 120 may extend outwardly from the bladder 114. For example, the valve 120 may extend from the bladder 114, through a portion of the porous material 110, and through the fluid impermeable barrier 102 thereby allowing a user (e.g., medical practitioner or patient) of the fluid collection assembly 100 easily access to the valve 120. As shown, the valve 120 may extend a short distance only from the fluid impermeable barrier 102, such as about 2 cm or less, about 1.5 cm or less, about 1 cm or less, about 0.75 cm or less, about 0.5 cm or less, about 0.25 cm or less, or in ranges of about 0.25 cm to about 0.75 cm, about 0.5 cm to about 1 cm, about 0.75 cm to about 1.5 cm, or about 1 cm to about 2 cm. However, the valve 120 may extend a significant distance from the fluid impermeable barrier 102, such as a distance that is about 2 cm or greater, about 5 cm or greater, about 10 cm or greater, about 50 cm or greater, about 100 cm or greater, about 500 cm or greater, about 1 m or greater, about 2 m or greater, or in ranges of about 2 cm to about 10 cm, about 5 cm to about 50 cm, about 10 cm to about 100 cm, about 50 cm to about 500 cm, about 100 cm to about 1 m, or about 500 cm to about 2 m. When the valve 120 extends a significant distance from the fluid impermeable barrier 102, the valve 120 may include a flexible tube which allows a user of the fluid collection assembly 100 to easily access to the valve 120 while the fluid collection assembly 100 is positioned adjacent to the pubic region without having the user near the pubic region (which the patient may find uncomfortable).

In an embodiment, as illustrated, the valve 120 extends from or near a back surface 122 of the fluid impermeable barrier 102. The back surface 122 of the fluid impermeable barrier 102 is the surface of the fluid impermeable barrier 102 opposite the opening 104. The valve 120 at or near the back surface 122 may allow a user of the fluid collection assembly 100 to access the valve 120 when the fluid collection assembly 100 is adjacent to the pubic region since, generally, the pubic region and the inner thighs of the patient may contact or obstruct the surfaces of the fluid impermeable barrier 102 except the back surface 122. Further, the valve 120 at or near the back surface 122 prevents the valve 120 from pressing against the pubic region and the inner thighs during use which may cause discomfort.

In an embodiment, the fluid collection assembly 100 may only include a single bladder 114 and/or a single valve 120. In an embodiment, the fluid collection assembly 100 may include a plurality of bladders 114 and/or a plurality of valves 120. For example, as illustrated, the fluid collection assembly 100 may include two bladders 114 on each lateral side of the fluid collection assembly 100 which allows the fluid collection assembly 100 to increase is size laterally which allows the fluid collection assembly 100 to contact the thighs of the patient. Each bladder 114 may include one or more valves 120 to allow for independent inflation of the bladders 114 which allows for better control of the shape and size of the fluid collection assembly 100. However, the fluid collection assembly 100 may only include a single valve 120 for two or more bladders 114. In some examples, a single bladder 114 may include a plurality of valves 120, for instance, to increase the likelihood that one valve 120 is easily accessible.

The inflation device 112 may include additional components other than the components discussed above. For example, the inflation device 112 may include less flexible material (e.g., rigid material or material that is less flexible than the walls 116) that are used to control the shape of the bladder 114 when the bladder 114 is inflated (e.g., switched from the first state to the second state). The less flexible material may form parts of the walls 116, wrap around the walls 116, or extend in the inflation region 118 between opposing portions of the walls 116 which limits expansion of the walls 116 at and near the less flexible material.

The at least one inflation fluid added or removed from the interior region 118 may include any suitable fluid, such as any suitable liquid or any suitable gas. In an embodiment, the inflation fluids are formed from a generally regarded as safe ("GRAS") material. Forming the inflation fluids from a GRAS materials may decrease health risks caused by inadvertently exposing the patient to the inflation fluids. Examples of GRAS materials that may form the inflation fluids includes water, saline solution, alcohol solution, atmospheric air, nitrogen, any other GRAS material, or combinations thereof.

As previously discussed, the fluid collection assembly 100 includes a fluid impermeable barrier 102. In the illustrated embodiment, the fluid impermeable barrier 102 is distinct from the inflation device 112 and is spaced from the inflation device 112 by at least a portion of the porous material 110.

The fluid impermeable barrier 102 may be formed of any suitable fluid imporous material(s), such as a fluid impermeable polymer (e.g., silicone, polypropylene, polyethylene, polyethylene terephthalate, a polycarbonate, etc.), a metal film, natural rubber, another suitable material, or combinations thereof. The fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least a surface of the fluid impermeable barrier 102 that may contact the patient may be formed from a soft and/or smooth material (e.g., silicone), thereby reducing chaffing. In an embodiment, the fluid impermeable barrier 102 may be formed from a flexible material, such as silicone, which allows the fluid impermeable barrier 102 to be bent into a shape that conforms the anatomy of the individual. Further, as shown in FIGS. 1B and 1C, forming the fluid impermeable barrier 102 from a flexible material allows the fluid impermeable barrier 102 to accommodate the shape and/or size changes by switching the fluid collection assembly 100 and the bladder 114 between states.

The fluid impermeable barrier 102 may define a hole that allows the valve 120 to extend through the fluid impermeable barrier 102. For example, the fluid impermeable barrier 102 may define the hole at or near the back surface 122 thereof. The hole formed in the fluid impermeable barrier 102 is configured to form a substantially fluid tight seal against the valve 120 or a sealant is applied between the fluid impermeable barrier 102 and the valve 120 to prevent bodily fluids from leaking through the hole.

In some examples, the fluid impermeable barrier 102 may be tubular (ignoring the opening), such as substantially cylindrical (as shown), oblong, prismatic, or flattened tubes when the bladder 114 is in the first state and/or the second state. During use, the outer surface 124 of the fluid impermeable barrier 102 may contact the patient. The fluid impermeable barrier 102 may be sized and shaped to fit in the gluteal cleft between the legs of a female user when the bladder 114 are in at least the second state.

The opening 104 provides an ingress route for fluids to enter the chamber 106. The opening 104 may be defined by the fluid impermeable barrier 102 such as by an inner edge of the fluid impermeable barrier 102. For example, the opening 104 is formed in and extends through the fluid impermeable barrier 102, from the outer surface 124 to the inner surface 126, thereby enabling fluid(s) to enter the chamber 106 from outside of the fluid collection assembly 100. The opening 104 may be an elongated hole in the fluid impermeable barrier 102. For example, the opening 104 may be defined as a cut-out in the fluid impermeable barrier 102. The opening 104 may be located and shaped to be positioned adjacent to a female urethra.

The fluid collection assembly 100 may be positioned proximate to the female urethral opening and urine may enter the chamber of the fluid collection assembly 100 via the opening 104. The fluid collection assembly 100 is configured to receive the fluid(s) into the chamber 106 via the opening 104. When in use, the opening 104 may have an elongated shape that extends from a first location below the urethral opening (e.g., at or near the anus or the vaginal opening) to a second location above the urethral opening (e.g., at or near the top of the vaginal opening or the pubic hair).

The opening 104 may have an elongated shape because the space between the legs of a female is relatively small when the legs of the female are closed, thereby only permitting the flow of the fluid(s) along a path that corresponds to the elongated shape of the opening 104 (e.g., longitudinally extending opening). The opening 104 in the fluid impermeable barrier 102 may exhibit a length measured along the longitudinal axis of the fluid collection assembly 100 that may be at least about 10% of the length of the fluid collection assembly 100, such as about 25% to about 50%, about 40% to about 60%, about 50% to about 75%, about 65% to about 85%, or about 75% to about 95% of the length of the fluid collection assembly 100.

The opening 104 in the fluid impermeable barrier 102 may exhibit a width measured transverse to the longitudinal axis of the fluid collection assembly 100 that may be, when the fluid collection assembly 100 and the bladder 114 are in the first state, at least about 10% of the circumference of the fluid collection assembly 100, such as about 25% to about 50%, about 40% to about 60%, about 50% to about 75%, about 65% to about 85%, or about 75% to about 100% of the circumference of the fluid collection assembly 100. The opening 104 may exhibit a width that is greater than 50% of the circumference of the fluid collection assembly 100 since the vacuum (e.g., suction) through the conduit 128 pulls the fluid through the porous material 110 and into the conduit 128. As shown in FIGS. 1B and 1C, switching the bladder 114 from the first state to the second state increases the width of the opening 104. The increased width of the opening 104 may allow the opening 104 to receive more bodily fluids than if the opening 104 did not exhibit the increased width.

In some examples, the opening 104 may be vertically oriented (e.g., having a major axis parallel to the longitudinal axis of the fluid collection assembly 100). In some examples (not shown), the opening 104 may be horizontally oriented (e.g., having a major axis perpendicular to the longitudinal axis of the fluid collection assembly 100). In an example, the fluid impermeable barrier 102 may be configured to be attached to the individual, such as adhesively attached (e.g., with a hydrogel adhesive) to the individual. According to an example, a suitable adhesive is a hydrogel layer.

As previously discussed, the fluid impermeable barrier 102 may define fluid outlet 108 configured to remove bodily fluids from the chamber 106. The fluid outlet 108 is distinct from the opening 104 and the valve 120. In some examples, the fluid outlet 108 is sized to receive the conduit 128. The conduit 128 may be disposed in the chamber 106 via the fluid outlet 108. The fluid outlet 108 may be sized and shaped to form an at least substantially fluid tight seal against the conduit 128 or the at least one tube substantially preventing the bodily fluids from escaping the chamber 106.

The fluid impermeable barrier 102 may include markings thereon, such as one or more markings to aid a user in aligning the fluid collection assembly 100 on the patient. For example, a line on the fluid impermeable barrier 102 (e.g., opposite the opening 104) may allow a healthcare professional to align the opening 104 over the urethral opening of the patient. In examples, the markings may include one or more of alignment guide or an orientation indicator, such as a stripe or hashes. Such markings may be positioned to align the fluid collection assembly 100 to one or more anatomical features such as a pubic bone, etc.

As previously discussed, the fluid collection assembly 100 includes porous material 110 disposed in the chamber 106. The porous material 110 may cover at least a portion (e.g., all) of the opening 104. The porous material 110 is exposed to the environment outside of the chamber 106 through the opening 104. The permeable properties referred to herein may be wicking, capillary action, absorption, diffusion, or other similar properties or processes, and are referred to herein as "permeable" and/or "porous." The porous material 110 may also wick the bodily fluids generally towards an interior of the chamber 106, as discussed in more detail below. The porous material 110 may include one or more of a fluid permeable membrane 130 or a fluid permeable support 132.

In an embodiment, at least a portion of the porous material 110 may be a wicking material configured to wick and/or allow transport of the bodily fluids away from the opening 104, thereby preventing bodily fluids from escaping the chamber 106. The porous material 110 may not include absorption of the bodily fluids into the w porous material 110. Put another way, substantially no absorption of the bodily fluids into the porous material 110 may take place after the wicking material is exposed to the bodily fluids. While no absorption is desired, the term "substantially no absorption" may allow for nominal amounts of absorption of the bodily fluids into the wicking material (e.g., absorbency), such as about 30 wt % or less of the dry weight of the wicking material, about 20 wt % or less, 10 wt % or less, about 7 wt % or less, about 5 wt % or less, about 3 wt % or less, about 2 wt % or less, about 1 wt % or less, or about 0.5 wt % or less of the dry weight of the wicking material.

The fluid collection assembly 100 may include the fluid permeable membrane 130 disposed in the chamber 106. The fluid permeable membrane 130 may cover at least a portion (e.g., all) of the opening 104. The fluid permeable membrane 130 may be composed to pull/push the bodily fluids away from the opening 104, thereby promoting fluid flow into the chamber 106, prevent fluid remaining on the vulva of the patient, and preventing the bodily fluids from escaping the chamber 106.

The fluid permeable membrane 130 may include any material that may be permeable to the bodily fluids. For example, the fluid permeable membrane 130 may include fabric, such as a gauze (e.g., a silk, linen, or cotton gauze), another soft fabric, or another smooth fabric. Forming the fluid permeable membrane 130 from gauze, soft fabric, and/or smooth fabric may reduce chaffing caused by the fluid collection assembly 100 and makes wearing the fluid collection assembly 100 more comfortable. In an embodiment, the fluid permeable membrane 130 is formed from a flexible material, such as gauze, since the shape and/or size of the fluid permeable membrane 130 may change when the fluid collection assembly 100 and the bladder 114 switch between states, as shown in FIGS. 1B and 1C. In an embodiment, the fluid permeable membrane 130 may define a plurality of perforations or may be continuous (e.g., does not define perforations). In an embodiment, the fluid permeable membrane 130 defines at least one hole that is configured to allow the valve 120 to extend through the fluid permeable membrane 130.

The fluid collection assembly 100 may include the fluid permeable support 132 disposed in the chamber 106. The fluid permeable support 132 is configured to support the fluid permeable membrane 130 and maintain the shape of the chamber 106 since the fluid impermeable barrier 102 and the fluid permeable membrane 130 may be formed from a relatively foldable, flimsy, or otherwise easily deformable material. For example, the fluid permeable support 132 may be positioned so the fluid permeable membrane 130 is disposed between the fluid permeable support 132 and the fluid impermeable barrier 102. The fluid permeable support 132 may support and maintain the position of the fluid permeable membrane 130 and the shape of the chamber 106. The fluid permeable support 132 may include any material that may be permeable to the bodily fluids, such as any of the fluid permeable membrane 130 materials disclosed above. For example, the fluid permeable membrane 130 material(s) may be utilized in a more dense or rigid form than in the fluid permeable membrane 130 when used as the fluid permeable support 132. The fluid permeable support 132 may be formed from any fluid porous material that is less deformable than the fluid permeable membrane 130. For example, the fluid permeable support 132 may include a porous polymer (e.g., nylon, polyester, polyurethane, polyethylene, polypropylene, etc.) structure (e.g., spun fibers such as spun nylon fibers), nonwoven material, or a foam (e.g., an open cell foam). In some examples, the fluid permeable support 132 may be formed from a natural material, such as cotton, wool, silk, or combinations thereof. In such examples, the material may have a coating to prevent or limit absorption of the bodily fluids into the material, such as a water repellent coating. In some examples, the fluid permeable support 132 may be formed from fabric, felt, gauze, or combinations thereof.

In an embodiment, as illustrated, the bladder 114 is positioned between the fluid permeable membrane 130 and the fluid permeable support 132 (e.g., the bladder 114 is positioned in the chamber 106). The bladder 114 may be positioned between the fluid permeable membrane 130 and the fluid permeable support 132 since that at least some materials that form the fluid impermeable barrier 102 and the fluid permeable membrane 130 exhibit a flexibility that allows the fluid impermeable barrier 102 and the fluid permeable membrane 130 to accommodate the size and/or shape changes discussed above. The fluid permeable membrane 130 also covers the bladder 114 thereby protecting the bladder 114 from objects that may puncture the bladder 114. The fluid impermeable barrier 102 may also cover at least a portion of the bladder 114 thereby also protecting the bladder 114 from objects. The bladder 114 may be positioned in the chamber 106 so the bladder 114 does not obstruct or only slight obstructs bodily fluids from flowing through the fluid permeable membrane 130 to the fluid permeable support 132. For example, the bladder 114 may be positioned so, at most, only a small portion of the bladder 114 (e.g., at most 20%, at most 10%, or at most 5%) is not positioned between the fluid impermeable barrier 102 and the support 132.

In some examples, the fluid permeable membrane 130 may be optional. For example, the porous material 110 may include only the fluid permeable support 132. In such examples, the bladder 114 may be positioned within the fluid permeable support 132 since, for instance, at least some materials of the support 132 disclosed herein are flexible enough to accommodate the shape and/or size changes discussed herein. In some examples, the fluid permeable support 132 may be optionally omitted from the fluid collection assembly 100 and the porous material 110 may only include the fluid permeable membrane 130. In such examples, the bladder 114 may be positioned within the fluid permeable membrane 130.

In an embodiment, the fluid permeable membrane 130 and/or the fluid permeable support 132 are wicking materials. In such an embodiment, the fluid permeable support 132 may have a greater ability to wick the bodily fluids than the fluid permeable membrane 130, such as to move the bodily fluids inwardly from the fluid permeable membrane 130. In some examples, the wicking ability of the fluid permeable support 132 and the fluid permeable membrane 130 may be substantially the same. In an embodiment, the fluid permeable membrane 130 and/or the fluid permeable support 132 are non-wicking materials (e.g., absorbent and/or adsorbent materials).

In an embodiment, not shown, the fluid permeable membrane 130 and the fluid permeable support 132 may at least substantially completely fill the portions of the chamber 106 not occupied by the inflation device 112 and the conduit 128. In an embodiment, as shown in FIG. 1D, the fluid permeable membrane 130 and the fluid permeable support 132 may not substantially completely fill the portions of the chamber 106 not occupied by the inflation device 112 or the conduit 128. In such an embodiment, the fluid collection assembly 100 includes the fluid reservoir 133 disposed in the chamber 106.

The fluid reservoir 133 is a substantially unoccupied portion of the chamber 106. The fluid reservoir 133 may be defined between the fluid impermeable barrier 102 and at least one of the inflation device 112, the fluid permeable membrane 130, or the fluid permeable support 132. The bodily fluids in the chamber 106 may flow through the fluid permeable membrane 130 and/or fluid permeable support 132 to the fluid reservoir 133. The fluid reservoir 133 may retain of the bodily fluids. The bodily fluids in the chamber 106 may flow through the fluid permeable membrane 130 and/or fluid permeable support 132 and, optionally, to the fluid reservoir 133. The fluid impermeable barrier 102 may retain the bodily fluids in the fluid reservoir 133. The fluid reservoir 133 may be in a portion of the chamber 106 designed to be in a gravimetrically low point of the fluid collection assembly 100 when the fluid collection assembly 100 is worn.

Figure 2A:
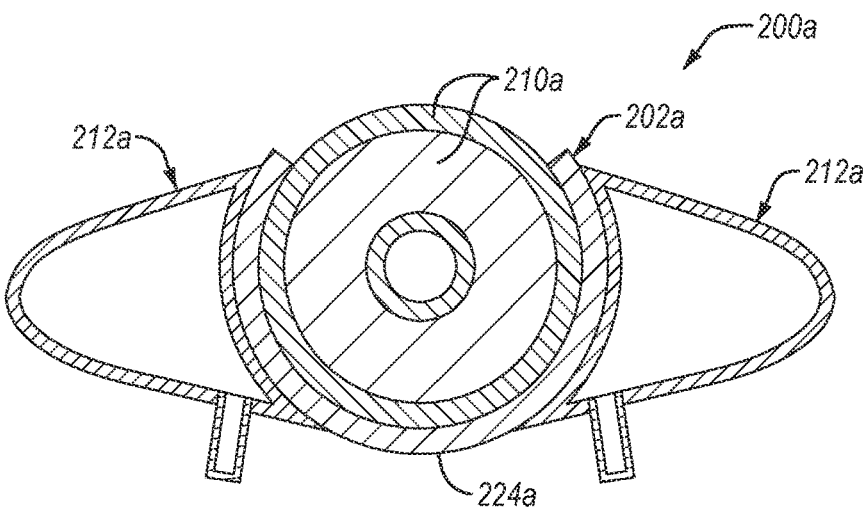
FIGS. 2A to 2C are schematic cross-sectional views of different fluid collection assemblies that each have inflation devices positioned differently, according to different embodiments.
Figure 2B:
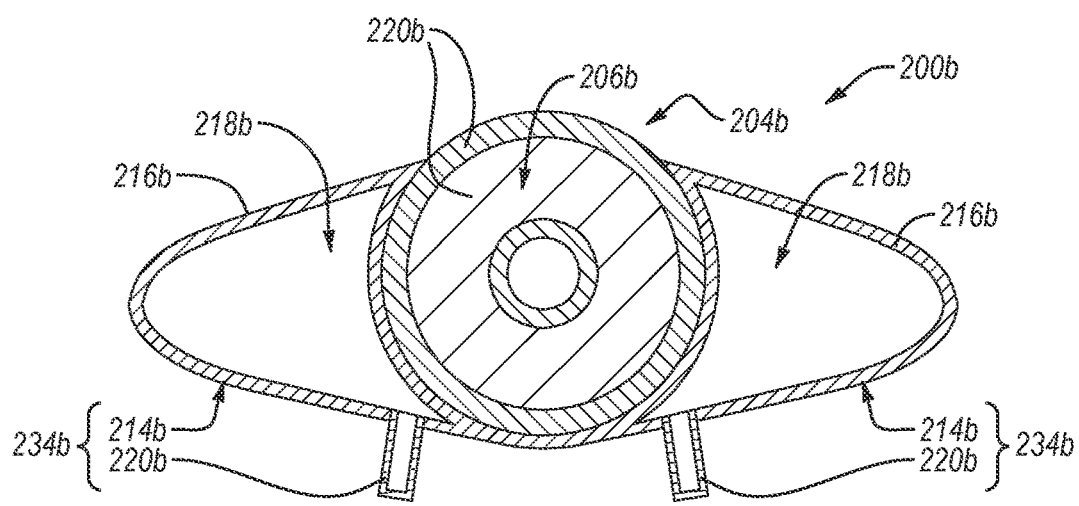
Figure 2C:
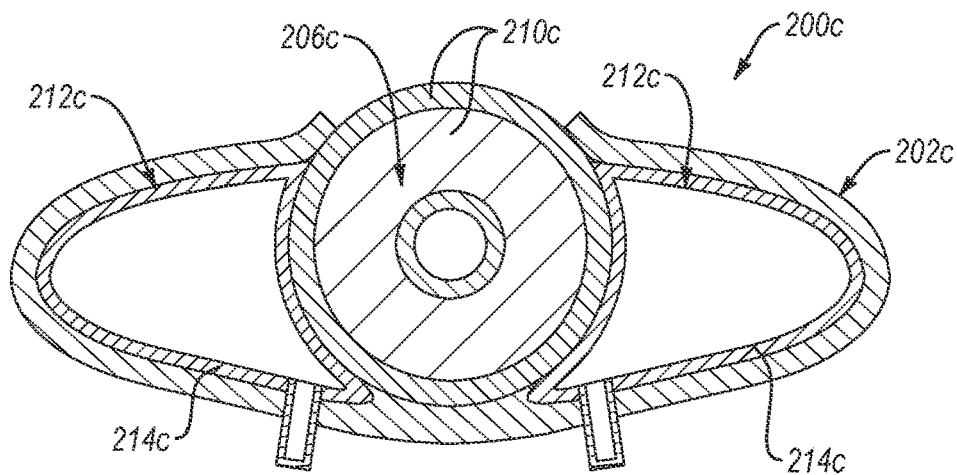

The inflation devices disclosed herein may be positioned in locations of the fluid collection assemblies disclosed herein other than between the fluid permeable membrane and the fluid permeable support. For example, FIGS. 2A to 2C are schematic cross-sectional views of different fluid collection assemblies that each have the inflation devices positioned differently, according to different embodiments. Except as otherwise disclosed herein, the fluid collection assemblies illustrated in FIGS. 2A-2C may be the same or substantially similar to any of the fluid collection assemblies disclosed herein. For example, the fluid collection assemblies illustrated in FIGS. 2A-2C may include a fluid impermeable barrier defining an opening, chamber, and fluid outlet; at least one porous material; and a conduit.

Referring to FIG. 2A, a fluid collection assembly 200a includes a fluid impermeable barrier 202a and at least one porous material 210a. The fluid impermeable barrier 202a includes an outer surface 224a. The fluid collection assembly 200a includes an inflation device 212a that is distinct from the fluid impermeable barrier 202a. The inflation device 212a is positioned on and attached to at least a portion of the outer surface 224a. For example, the inflation device 212a may be attached to the outer surface 224a using an adhesive, ultrasonic welding, heat staking, or any other suitable technique. Since the inflation device 212a is disposed on the outer surface 224a, switching the fluid collection assembly 202a and the inflation device 212a between different states will have limited effect on the size and shape of the fluid impermeable barrier 202a and the porous material 210a compared to the fluid impermeable barrier 102 and the fluid permeable membrane 130 shown in FIGS. 1A-1D. The fluid impermeable barrier 202a and the porous material 210a may, optionally, be formed from more rigid materials than the fluid impermeable barrier 102 and the fluid permeable membrane 130 shown in FIGS. 1A-1D. Positioning the inflation device 212a on the outer surface 224a may make manufacturing of the fluid collection assembly 200a easier since the inflation device 212a need not be positioned between two components of the fluid collection assembly 200a.

Referring to FIG. 2B, the fluid collection assembly 200b includes an inflation barrier 234b. The inflation barrier 234b is a fluid impermeable barrier and an inflation device integrally formed together. The inflation barrier 234b may exhibit any of the properties and functions as any of the fluid impermeable barriers and inflation devices disclosed herein. For example, the inflation barrier 234b may define an opening 204b, a chamber 206b, and a fluid outlet (not shown) and may be configured to prevent bodily fluids from leaking from the chamber 206b. The inflation barrier 234b may also include a bladder 214b and a valve 220b. The bladder 214b includes one or more walls 216b defining an interior region 218b. The inflation barrier 234b is configured to switch between one or more states (e.g., a first state and a second state) by adding or removing fluids from an inflation region 218 using the valve 220.

Switching the fluid collection assembly 202b and the inflation barrier 234b between different states will have limited effect on the size and shape of the porous material 210b compared to the fluid impermeable barrier 130 shown in FIGS. 1A-1C. The porous material 210b may, optionally, be formed from more rigid materials than the fluid permeable membrane 130 shown in FIGS. 1A-1C. Further, the inflation barrier 234b may make manufacturing of the fluid collection assembly 200b easier since the inflation barrier 234b need not be positioned between two components of the fluid collection assembly 200b and decreases the number of components that form the fluid collection assembly 200b.

Referring to FIG. 2C, the fluid collection assembly 200c includes a fluid impermeable barrier 202c and at least one porous material 210c. The fluid collection assembly 200c also includes an inflation device 212c that is distinct from the fluid impermeable barrier 202c. At least a portion of the inflation device 212c (e.g., at least the bladder 214c) is positioned between the fluid impermeable barrier 202c and the porous material 210c. The fluid impermeable barrier 202c may protect the inflation device 212c from objects that may puncture the inflation device 212c. Since the inflation device 212c is disposed between the fluid impermeable barrier 202c and the porous material 210c, switching the fluid collection assembly 202c and the inflation device 212c between different states will have limited effect on the size and shape of the porous material 210c compared to the porous material 110 shown in FIGS. 1A-1D. The porous material 210c may, optionally, be formed from more rigid materials than the fluid permeable membrane 130 shown in FIGS. 1A-1D. Positioning the inflation device 212c between the fluid impermeable barrier 202c and the porous material 210c may make manufacturing of the fluid collection assembly 200c easier since the inflation device 212c may be positioned in the chamber 206c before or while the porous material 210c is positioned in the chamber 206c. The method for forming the fluid collection assembly 200c does not require the additional step of positioning the inflation device 212c in the porous material 210c.

It is noted that the inflation devices disclosed herein may have positions other that the positions illustrated in FIGS. 1B and 2A-2C. For example, the inflation devices may be positioned within the fluid permeable membrane, within the fluid permeable support, between the fluid permeable support and the conduit, within the conduit, or integrally formed with the conduit.

Figure 3:
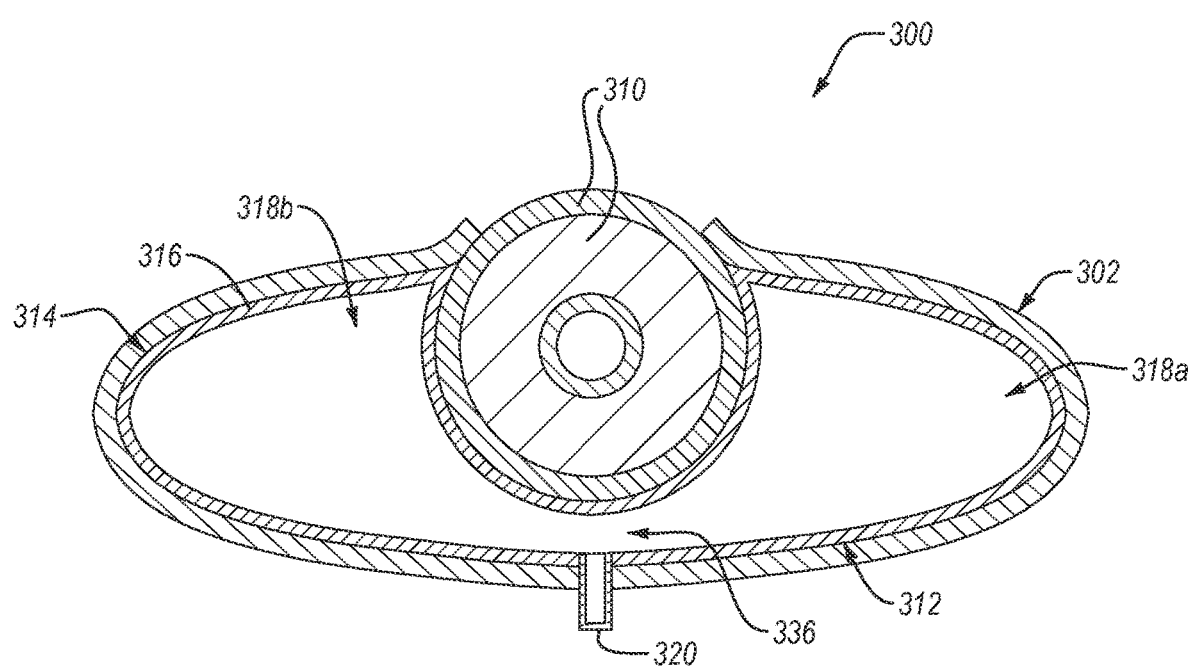
FIG. 3 is a cross-sectional schematic view of a fluid collection assembly when the at least one bladder thereof is in the second state, according to an embodiment.

FIG. 3 is a cross-sectional schematic view of a fluid collection assembly 300 when the at least one bladder thereof is in the second state, according to an embodiment. Except as otherwise disclosed herein, the fluid collection assembly 300 is the same or substantially similar to any of the fluid collection assemblies disclosed herein. For example, the fluid collection assembly 300 includes a fluid impermeable barrier 302 and at least one porous material 310. The fluid collection assembly 300 also includes at least one inflation device 312. In an embodiment, as illustrated, at least a portion of the inflation device 312 is positioned between the fluid impermeable barrier 302 and the porous material 310. However, the inflation device 312 may include any of the other positions disclosed herein.

The inflation device 312 includes a bladder 314. The first bladder 314 includes one or more walls 316. The one or more walls 316 define a first inflation region 318a and a second inflation region 318b. The inflation device 312 includes at least one passageway 336 extending between and fluidly coupling the first inflation region 318a to the second inflation region 318b. For example, the one or more walls 316 defines the passageway 336. Inflation fluids present in the first inflation region 318a may flow to the second inflation region 318b by entering the passageway 336, flowing through the passage way 336, and then exiting the passageway 336 and vice versa. The pressure inside each of the first inflation region 318a and the second inflation region 318b remains the same thereby preventing over inflation or under inflation of one of the first inflation region 318a or the second inflation region 318b.

In an embodiment, the inflation device 312 may include a single valve 320 since the first inflation region 318a is in fluid communication with the second inflation region 318b. The valve 320 may be in direct fluid communication with one of the first inflation region 318a, the second inflation region 318b, or the passageway 336. However, it is noted that the inflation device 312 may include at least one valve 320 that is in direct fluid communication with at least two of the first inflation region 318a, the second inflation region 318b, or the passageway 336.

In an embodiment, inflation device 310 may include one or more additional inflation regions (not shown) that are in fluid communication with the first inflation region 318a and the second inflation region 318b through the passageway 336 or through one or more additional passageways. In an embodiment, the passageway 336 may include a passageway valve that selective permits or restricts fluid flow between the first inflation region 318a to the second inflation region 318b. For example, the passageway valve may be open (e.g., permit fluid flow between the first inflation region 318a and the second inflation region 318b) when it is desirable for the first inflation region 318a and the second inflation region 318b to exhibit the same pressure. However, the passageway valve may be closed when it is desirable to independently inflate at least one of the first inflation region 318a or the second inflation region 318b (e.g., when it is desirable for one of the first inflation region 318a or the second inflation region 318b to be inflated more than the other). The passageway valve may include any suitable valve, such as a mechanical valve or a clamp.

Figure 4A:
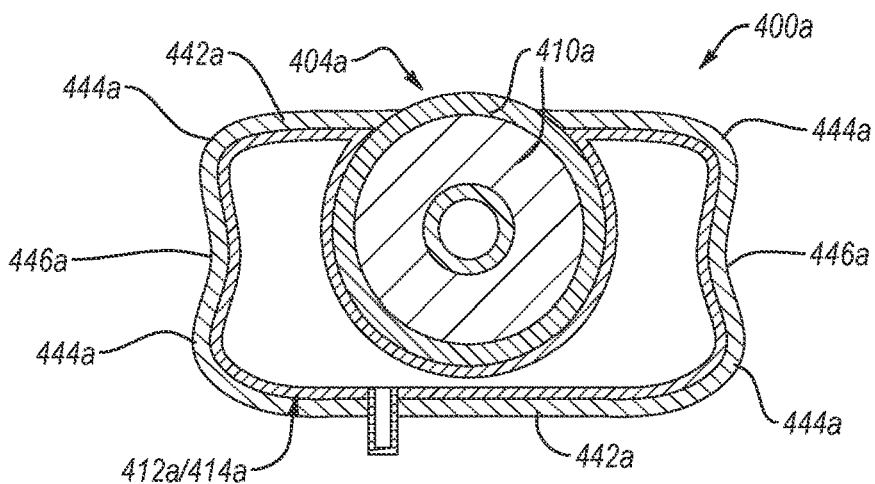
FIGS. 4A to 4C are schematic cross-sectional views of fluid collection assemblies exhibiting different shapes when the bladders of the fluid collection assemblies are in the second state, according to different embodiments.
Figure 4B:
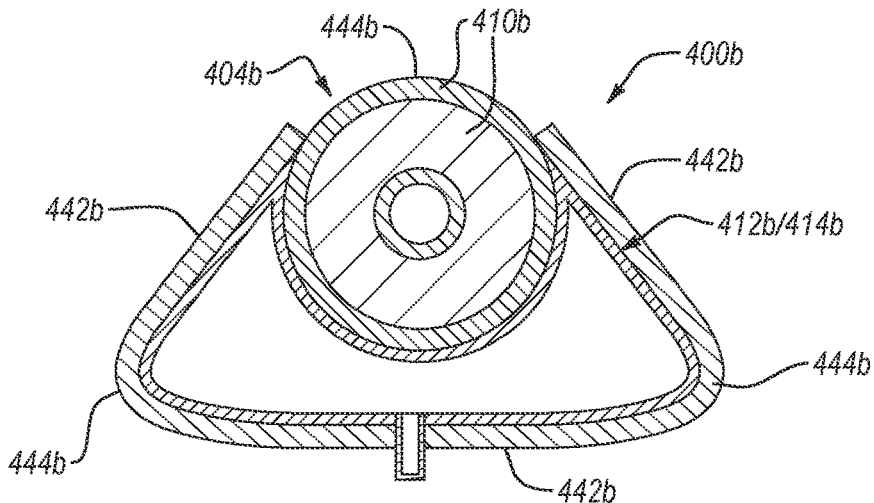
Figure 4C:
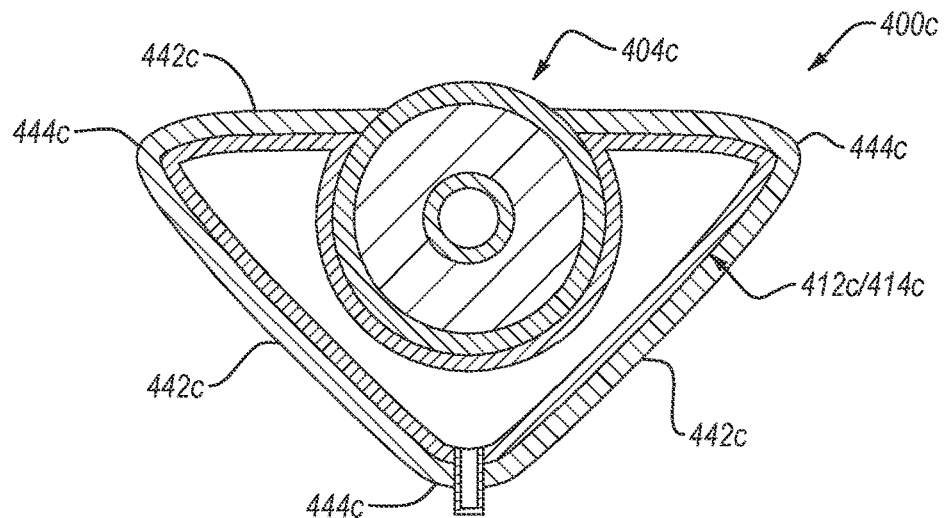

The fluid collection assemblies illustrated in FIGS. 1C and 2A-3 exhibit the same general oblong cross-sectional shape when the bladders of the fluid collection assemblies are in the second state. However, it is noted that the fluid collection assemblies may exhibit other cross-sectional shapes, without limitation. FIGS. 4A to 4C are schematic cross-sectional views of fluid collection assemblies exhibiting different shapes when the bladders of the fluid collection assemblies are in the second state, according to different embodiments. Except as otherwise disclosed herein, the fluid collection assemblies illustrated in FIGS. 4A-4C are the same or substantially similar to any of the fluid collection assemblies disclosed herein. For example, the fluid collection assemblies include fluid impermeable barrier, at least one porous material, and at least one inflation device. In an embodiment, as illustrated, the inflation device is positioned between the fluid impermeable barrier and the porous material. However, it is noted that the inflation device may have any of the positions disclosed herein.

Regarding FIG. 4A, a fluid collection assembly 400a includes an inflation device 412a. The inflation device 412a includes at least one bladder 414a. When the bladder 414a is in the second state, the fluid collection assembly 400a exhibits a generally hour-glass cross-sectional shape. Similarly, when the bladder 414a is in the second state, the bladder 414a may form a generally hour-glass cross-sectional shape that corresponds to the generally hour-glass cross-sectional shape of the fluid collection assembly 400a except that the bladder 414a defines a cutout in which some components of the fluid collection assembly 400a (e.g., the at least one porous material 410a) may be positioned. In an embodiment, as illustrated, the bladder 414a includes a plurality of bladders each in fluid communication with each other. In an embodiment, the bladder 414a may include a plurality of bladders not in fluid communication with each other. In an embodiment, the bladder 414a may include a single bladder.

The generally hour-glass shape of the fluid collection assembly 400a includes two opposing edges 442a, four apexes 444a at the ends of the edges 442a, and two concave surfaces 446a extending between adjacent apexes 444a. The opening 404a is formed on one edge 442a. The two apexes 444a that are most proximate to the opening 404a are configured to fit at least partially in the fold formed between the inner thighs and the rest of the pubic region of the patient. The concave surfaces 446a are configured to press against and generally correspond to the convex shape inner thighs of the patient. The ability of the two apexes 444a to fit at least partially into the fold formed between the inner thighs and the rest of the pubic region and the concave surfaces 446a to correspond to the concave inner thighs help secure the fluid collection assembly 400a to the patient, maintain the opening 404a against the vulva of the patient, and make the fluid collection assembly 400a more comfortable compared to some other shapes.

Regarding FIG. 4B, a fluid collection assembly 400b includes an inflation device 412b. The inflation device 412b includes at least one bladder 414b. When the bladder 414b is in the second state, the fluid collection assembly 400b exhibits a generally triangular cross-sectional shape. Similarly, when the bladder 414b is in the second state, the bladder 414b may also form a generally triangular cross-sectional shape that corresponds to the generally triangular cross-sectional shape of the fluid collection assembly 400b except that the bladder 414b defines a cutout in which some components of the fluid collection assembly 400b (e.g., the at least one porous material 410b) may be positioned. In an embodiment, as illustrated, the bladder 414b may include a single bladder. In an embodiment, the bladder 414b includes a plurality of bladders each in fluid communication with each other. In an embodiment, the bladder 414b may include a plurality of bladders not in fluid communication with each other.

The generally triangular cross-sectional shape of the fluid collection assembly 400b includes three edges 442b and three apexes 444b at the intersection of each edge 442b. The opening 404b is formed at one of the three apexes 444b which allows that porous material 410b to partially fit between the labia and to press more closely to the urethral opening of the patent. Positioning a portion of the porous material 410b between the labia helps secure the fluid collection assembly 400b to the patient.

FIG. 4C illustrates a fluid collection assembly 400c that, except as otherwise disclosed herein, in the same as the fluid collection assembly 400b of FIG. 4B. For example, when the bladder 414c of the inflation device 412c is in the second state, the fluid collection assembly 400c exhibits a generally triangular cross-sectional shape and the bladder 414c exhibits a corresponding generally triangular cross-sectional shape with a cutout. However, the opening 404c is formed in one edge 442c. Forming the opening 404c allows two of the apexes 444c that are closest to the opening 404c to fit into the fold between the inner thighs and the rest of the pubic region. Fitting the edges 442c into the fold helps secure the fluid collection assembly 400c to the patient. Further, the two edges 442c that do not include the opening 404c better conform to the convex shape of the inner thighs of the patient compared to the fluid collection assembly 400b of FIG. 4B which may make the fluid collection assembly 400c more comfortable to use.

FIG. 5A is a schematic illustration of a first fluid collection assembly 500a being used with a first female patient 548a, according to an embodiment. During use, the first fluid collection assembly 500a is positioned between the thighs 552a of the first female patient 548a so the opening 504a of the first fluid collection assembly 500a is adjacent to the vulva 550a of the first female patient 548a. The first fluid collection assembly 500a may include any of the fluid collection assemblies disclosed herein that are configured to be used with a female patient. The thighs 552a of the first female patient 548a are sufficiently large that the first fluid collection assembly 500a presses against the thighs of the first female patient 548a even when the bladder of the first fluid collection assembly 500a is in the first state. The first fluid collection assembly 500a may be conformed to the vulva 550a and other portions of the pubic region of the first female patient 548a and the thighs 552a of the first female patient 548a may maintain the shape of the first fluid collection assembly 500a. The first fluid collection assembly 500a may be used with female patients whose thighs are sufficiently large that the first fluid collection assembly 500a need not be inflated even though the first fluid collection assembly 500a can be inflated.

FIG. 5B is a schematic illustrated of a second fluid collection assembly 500b being used with a second female patient 548b, according to an embodiment. During use, the second fluid collection assembly 500b is positioned between the thighs 552b of the second female patient 548b so the opening 504b of the second fluid collection assembly 500b is adjacent to the vulva 550b of the first female patient 548b. The second fluid collection assembly 500b is the same as the first fluid collection assembly 500a. The thighs 552b of the second female patient 548b are sufficiently small that the second fluid collection assembly 500b does not contact the thighs 552b or does not contact the thighs 552b with sufficient force to keep the second fluid collection assembly 500b conformed to the pubic region of the second female patient 548b. The bladder of the second fluid collection assembly 500b may be inflated from the first state to the second state. The second fluid collection assembly 500b is sufficiently inflated in the second state that the second fluid collection assembly 500b presses against the thighs 552b of the second female patient 548b with sufficient force that the thighs 552b keep the second fluid collection assembly 500b conformed to the pubic region. FIG. 5B illustrates how the fluid collection assemblies disclosed herein may be used with female patients that are underweight or have thin thighs.

Figure 6:
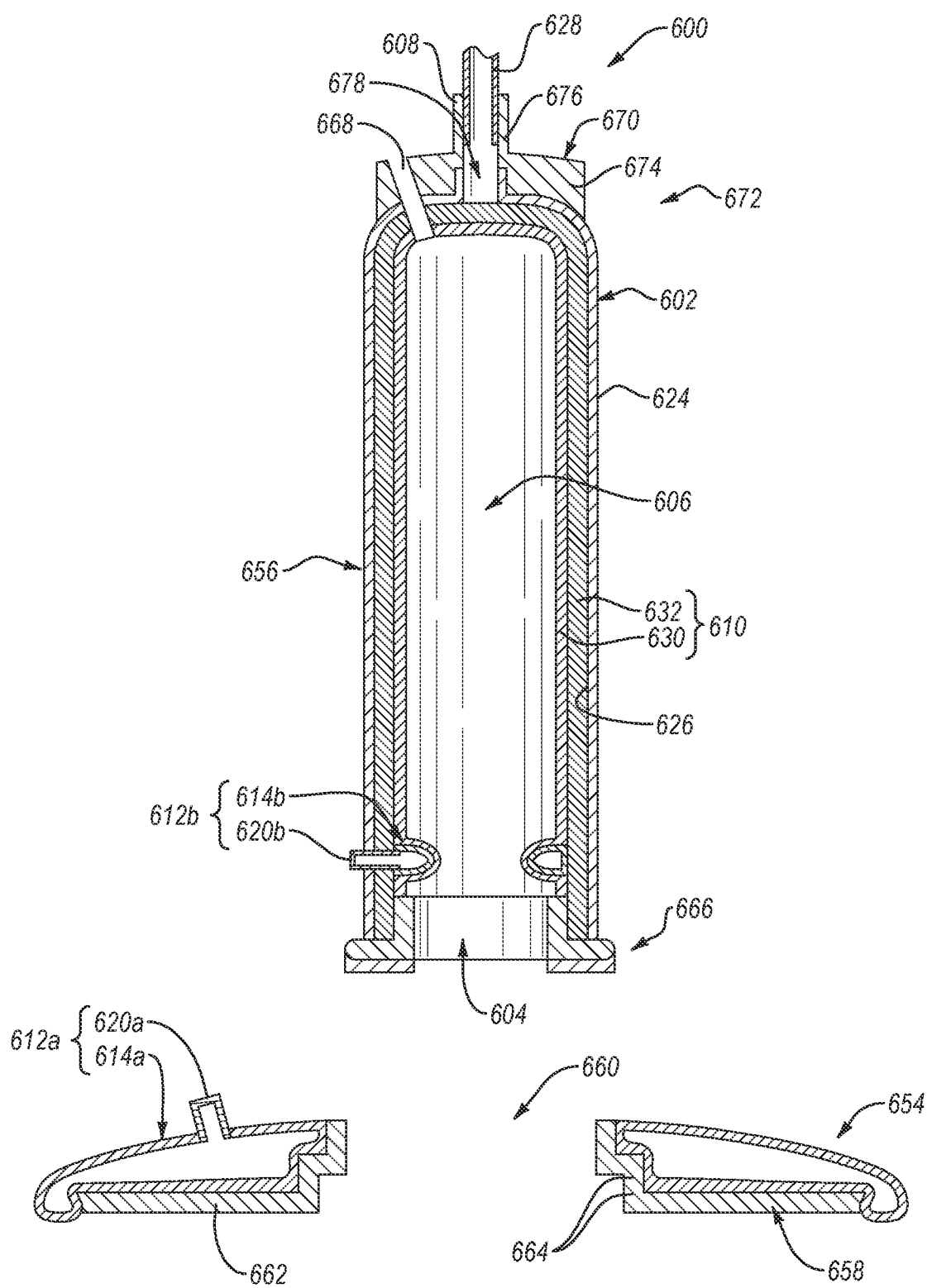
FIG. 6 is a cross-sectional view of a male fluid collection assembly, according to an embodiment.

The fluid collection assemblies shown in FIGS. 1A-5B are examples of female fluid collection assemblies configured to collect bodily fluids from females (e.g., collection urine from a female urethral opening). However, the fluid collection assemblies, systems, and method disclosed herein may include male fluid collection assemblies shaped, sized, and otherwise configured to collection bodily fluids from males (e.g., collection urine from a penis). FIG. 6 is a cross-sectional view of a male fluid collection assembly 600, according to an embodiment.

The fluid collection assembly 600 includes a receptacle 654 and a sheath 656. The receptacle 654 is sized, shaped, and made of a material to be coupled to skin that surrounds the penis (mons pubis, testicles, perineum, etc.) and have the penis positioned therethrough. For example, the receptacle 654 may include an annular base 658 that defines an opening 660 in the receptacle 654. The annular base 658 is sized and shaped to be positioned around the penis and have the penis positioned therethrough. The annular base 658 may also be sized, shaped, made of a material, or otherwise configured to be coupled (e.g., adhesively attached, such as with a hydrogel adhesive) to the skin around the penis. In an example, the annular base 658 may exhibit the general shape or contours of the skin surface that the annular base 658 is selected to be coupled with. The annular base 658 may be flexible thereby allowing the annular base 658 to conform to any shape of the skin surface. The annular base 658 may include a laterally extending flange 662. The receptacle 654 also defines a hollowed region configured to receive (e.g., seal against) the sheath 656. For example, the receptacle 654 may include a longitudinally extending flange 664 that extends upwardly from the annular base 658. The longitudinally extending flange 664 may be tall enough to prevent the sheath 656 from being accidentally removed from the receptacle 654 (e.g., at least 0.25 cm tall, 1 cm tall, at least 9 cm tall, or at least 5 cm tall). The receptacle 654 is at a proximal region 666 (regarding a patient) of the fluid collection assembly 600.

The sheath 656 includes (e.g., may be formed from) a fluid impermeable barrier 602 sized and shaped to fit into the hollowed region of the receptacle 654. For example, the sheath 656 may be generally tubular or cup-shaped, as shown. The generally tubular or cup-shaped fluid impermeable barrier 602 may at least partially define the outer surface 624 of the sheath 656. The fluid impermeable barrier 602 may be similar or identical to the fluid impermeable barrier 102 as disclosed herein, in one or more aspects. For example, the fluid impermeable barrier 602 may be constructed of any of the materials disclosed herein for the fluid impermeable barrier 102. The fluid impermeable barrier 602 at least partially defines the chamber 606. For example, the inner surface 626 of the fluid impermeable barrier 602 at least partially defines the perimeter of the chamber 606. The chamber 606 may be similar or identical to the chamber 106 in one or more aspects. For example, the chamber 606 may at least temporarily retain fluids. As shown, the fluid collection assembly 600 may include at least one porous material 610. The porous material 610 may be similar or identical to the porous material 110 in one or more aspects. For example, the porous material 610 may include one or more of a fluid permeable membrane 630 or a fluid permeable support 632. The fluid impermeable barrier 602 may also define an opening 604 extending through the fluid impermeable barrier 602 configured to have a penis positioned therethrough.

The sheath 656 and fluid impermeable barrier 602 may also include at least one aperture 668 (e.g., vacuum relief hole) that allows the chamber 606 to remain substantially at atmospheric pressure. The at least one aperture 668 may be at any point on the sheath 656, such as near or nearer the opening 660. In some examples (not shown), the aperture 668 may extend through the cap 670 or be disposed beneath the cap 670. In some examples, the fluid collection assembly 600 may not include the aperture 668, such as when a more complete seal as desired for the chamber 606.

The sheath 656 also includes at least a portion of the conduit 628, such as at least partially disposed in the chamber 606. For example, the conduit 628 may extend from the sheath 656 at the distal region 672 to a proximal region 666 at least proximate to the opening 660. The proximal region 666 may be disposed near or on the skin around the penis or pubic area therearound. When a patient lays on their back, bodily fluids may aggregate near the opening 660 against the skin of the patient. The bodily fluids may be removed from the chamber 606 via the conduit 628.

In some examples, the fluid impermeable barrier 602 may be constructed of a material and/or have a thickness that allows the sheath 656 to collapse when placed under vacuum, such as to remove air around a penis in the fluid collection assembly 600 during use. In such examples, the conduit 628 may extend only to or into the distal region 672 in the chamber 606 (e.g., not through to the area adjacent the opening). In such examples, bodily fluids may be collected and removed from the fluid collection assembly 600 at the end nearest the aperture 668. In such examples, the at least one aperture may be located nearest the opening 660.

In an example, portions of the chamber 606 may be substantially empty due to the varying sizes and rigidity of the male penis. However, in some examples, the outermost regions of the chamber 606 (e.g., periphery of the interior regions of the sheath 656) may include porous material 610 (e.g., one or more of the fluid permeable membrane 630 and fluid permeable support 632). For example, the porous material 610 may be bonded to the inner surface 626 of the fluid impermeable barrier 602. The porous material 610 may be positioned (e.g., at the distal end of the chamber 606) to blunt a stream of urine from the penis thereby limiting splashing and/or to direct the fluid(s) to a selected region of the chamber 606. Since the chamber 606 is substantially empty (e.g., substantially the chamber 606 forms a reservoir), the fluids are likely to pool at a gravimetrically low point of the chamber 606. The gravimetrically low point of the chamber 606 may be at an intersection of the skin of an patient and the fluid collection assembly 600, a corner formed in the sheath 656, or another suitable location depending on the orientation of the patient.

The porous material 610 may include one or more of the fluid permeable membrane 630 or the fluid permeable support 632. The fluid permeable membrane 630 and the fluid permeable support 632 may be similar or identical to the fluid permeable membrane 130 or the fluid permeable support 132 as respectively disclosed herein, in one or more aspects such as material make-up or wicking ability. One or more of the fluid permeable membrane 630 or the fluid permeable support 632 may be disposed between the fluid impermeable barrier 602 and a penis inserted into the chamber 606. The fluid permeable membrane 630 may be positioned between the fluid impermeable barrier 602 and a penis inserted into the chamber 606, such as between the fluid permeable support 632 and penis of a wearer as shown. The fluid permeable support 632 may be positioned between the fluid permeable membrane 630 and the fluid impermeable barrier 602. The inner surface 626, optionally including the end of the chamber 606 substantially opposite the opening 604, may be covered with one or both the fluid permeable membrane 630 or the fluid permeable support 632. The fluid permeable support 632 or the fluid permeable membrane 630 may be affixed (e.g., adhered) to the fluid impermeable barrier 602. The fluid permeable support 632 or the fluid permeable membrane 630 may be affixed to each other. In some examples, the porous material 610 only includes the fluid permeable membrane 630 or the fluid permeable support 632.

The fluid collection assembly 600 includes one or more inflation devices in one or more portions thereof. For example, the fluid collection assembly 600 will be discusses as having a first inflation device 612a and a second inflation device 612b. However, it is noted that the fluid collection assembly 600 may only include a single inflation device (e.g., the first inflation device 612a, the second inflation device 612b, or another inflation device) or three or more inflation devices (e.g., the first inflation device 612a, a second inflation device 612b, and another inflation device). The inflation devices of the fluid collection assembly 600 may be similar or identical to any of the inflation devices disclosed herein in one or more aspects. For example, the first inflation device 612a may include at least one first bladder 614a and at least one first valve 620a and the second inflation device 612b may include at least one second bladder 614b and at least one second valve 620b.

The first inflation device 612a may be disposed on (as shown) or in the receptacle 654. In an embodiment, the first inflation device 612a increases the width (measure perpendicular to the longitudinal axis of the fluid collection assembly 600) of the receptacle when the pubic region of the patient is large enough to accommodate the increased width. The increase width of the receptacle 654 increases the surface area of the receptacle 654 that contacts the patient which may facilitate securement of the receptacle 654. For example, the increased surface area may allow for additional adhesive to be applied to the surface of the receptacle 654 that contacts the patient. In an embodiment, the first inflation device 612a changes the cross-sectional shape (measured perpendicular to the longitudinal axis of the fluid collection assembly 600) of the receptacle 654 which allows the receptacle 654 to conform to differently shaped pubic regions. In an embodiment, the first inflation device 612a increases a thickness of the receptacle 654 which may increase a contact pressure that, at least partially, secures the receptacle 654 to the pubic region.

The second inflation device 612b may be disposed on or in (as shown) the sheath 656. The second inflation device 612b may be configured to decrease a width of the chamber 606. For example, decreasing the width of the chamber 606 may cause the sheath 656 to contact a smaller diameter penis, a non-erect penis, or to conform to a penis that is transitioning between erect and non-erect states. Decreasing the width of the chamber 606 may inhibit bodily fluids from flowing away from the fluid outlet 608 thereby facilitating removal of the bodily fluids from the chamber 606.

In some examples, the fluid collection assembly 600 includes a cap 670 at a distal region 672. The cap 670 defines an fluid outlet 608 through which the fluids may be removed from the fluid collection assembly 600. The fluid outlet 608 is in fluid communication with the chamber 606. The cap 670 may be disposed over at least a portion of the distal region 672 of one or more of the fluid impermeable barrier 602 or the porous material 610. The cap 670 may be made of a polymer, rubber, or any other fluid impermeable material. The cap 670 may be attached to one or more of the fluid impermeable barrier 602, the porous material 610, or the conduit 628. The cap 670 may have a laterally extending flange 674 and a longitudinally extending flange 676. The laterally extending flange 674 may cover at least a portion of the distal region 672 of the fluid collection assembly 600. The longitudinally extending flange 676 may laterally extend a distance from the sheath 656. The longitudinally extending flange 676 is sized and configured to receive and fluidly seal against the conduit 628, such as within the fluid outlet 608. The conduit 628 may extend a distance within or through the cap 670, such as to the porous material 610, through the porous material 610, or to a point set-off from the porous material 610. In an example, the cap 670 may define a reservoir 678.

The reservoir 678 is an unoccupied portion of device such as in the cap 670 and is void of other material. In some examples, the reservoir 678 is defined at least partially by the porous material 610 and the cap 670. During use, the fluids in the chamber 606 may flow through the porous material 610 to the reservoir 678. The reservoir 678 may store at least some fluids and/or position the fluids for removal by the conduit 628. In some examples, at least a portion of the porous material 610 may extend continuously between at least a portion of the opening of the fluid outlet 608 and chamber 606 to wick any fluid from the opening directly to the reservoir 678.

In some examples (not shown), the fluid impermeable barrier 602 may be disposed on or over the cap 670, such as enclosing the cap 670 within the chamber 606.

In some examples, the sheath 656 may include at least a portion of the conduit 628, such as at least partially disposed in the chamber 606. For example, the conduit 628 may extend from the sheath 656 to a region at least proximate to the opening 660. The inlet of the conduit 628 may be positioned adjacent to the annular base 658. The inlet of the conduit 628 may be positioned to be adjacent or proximate to the gravimetrically low point of the chamber 606, such as adjacent to the annular base 658. For example, the inlet may be co-extensive with or offset from the opening 660. In examples, the inlet may be positioned adjacent to the distal region 672 of the sheath 656 (e.g., substantially opposite the opening).

The proximal region 666 may be disposed near or on the skin around the penis and the inlet of the conduit 628 may be positioned in the proximal region 666. The outlet of the conduit 628 may be directly or indirectly coupled to a vacuum source. Fluid may be removed from the proximal region 666 of the chamber 606 via the conduit 628.

The receptacle 654, the sheath 656, the cap 670, and the conduit 628 may be attached together using any suitable method. For example, at least two of the receptacle 654, the sheath 656, the cap 670, or the conduit 628 may be attached using at least one of an interference fit, an adhesive, stitching, welding (e.g., ultrasonic welding), tape, any other suitable method, or combinations thereof.

In some examples (not shown), the fluid collection assembly 600 may have a one piece design, with one or more of the sheath 656, the receptacle 654, and the cap 670 being a single, integrally formed piece.

Figure 7:
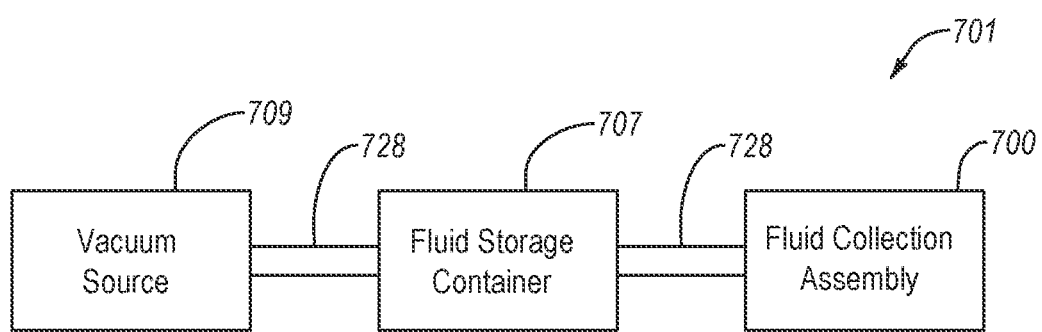
FIG. 7 is a block diagram of a system for fluid collection, according to an embodiment.

Also as shown, the conduit 628 may be at least partially disposed with the chamber of a fluid collection assembly. The conduit 628 may extend from the distal region 672 to the proximal region 666. For example, the conduit 628 may extend through the cap 670 to a point adjacent to the receptacle 654. The conduit 628 is sized and positioned to be coupled to a fluid storage container or the vacuum source (FIG. 7). An outlet of the conduit 628 may be operably coupled to the vacuum source, directly or indirectly. The inlet of the conduit 628 may be positioned within the chamber 606 such as at a location expected to be at the gravimetrically low point of the fluid collection assembly during use. By positioning the inlet in a location expected to be at the gravimetrically low point of the fluid collection assembly when worn by the user, fluids introduced into the chamber 606 may be removed via the conduit 628 to prevent pooling or stagnation of the fluid within the chamber 606.

In some examples, the vacuum source may be remotely located from the fluid collection assembly 600. In such examples, the conduit 628 may be fluidly connected to the fluid storage container, which may be disposed between the vacuum source and the fluid collection assembly 600.

During operation, a male using the fluid collection assembly 600 may discharge fluid(s) (e.g., urine) into the chamber 606. The fluid(s) may pool or otherwise be collected in the chamber 606. At least some of the fluid(s) may be pulled through the interior of the conduit 628 via the inlet. The fluid may be drawn out of the fluid collection assembly 600 via the vacuum/suction provided by the vacuum source. During operation, the aperture 668 may substantially maintain the pressure in the chamber 606 at atmospheric pressure even though fluid is introduced into and removed from the chamber 606.

Additional examples of male fluid collection assemblies that may include one or more inflation devices are disclosed in U.S. patent application Ser. No. 16/433,773 filed on Jun. 6, 2019, the disclose of which is incorporated herein, in its entirety, by this reference.

FIG. 7 is a block diagram of a system 701 for fluid collection, according to an embodiment. The system 701 includes a fluid collection assembly 700, a fluid storage container 707, and a vacuum source 709. The fluid collection assembly 700, the fluid storage container 707, and the vacuum source 709 may be fluidly coupled to each other via one or more conduits 728. For example, fluid collection assembly 700 may be operably coupled to one or more of the fluid storage container 707 or the vacuum source 709 via the conduit 728. Fluid (e.g., urine or other bodily fluids) collected in the fluid collection assembly 700 may be removed from the fluid collection assembly 700 via the conduit 728 which protrudes into the fluid collection assembly 700. For example, an inlet of the conduit 728 may extend into the fluid collection assembly 700, such as to a reservoir. The outlet of the conduit 728 may extend into the fluid collection assembly 700 or the vacuum source 709. Suction force may be introduced into the chamber of the fluid collection assembly 700 via the inlet of the conduit 728 responsive to suction (e.g., vacuum) force applied at the outlet of the conduit 728.

The suction force may be applied to the outlet of the conduit 728 by the vacuum source 709 either directly or indirectly. The suction force may be applied indirectly via the fluid storage container 707. For example, the outlet of the conduit 728 may be disposed within the fluid storage container 707 and an additional conduit 728 may extend from the fluid storage container 707 to the vacuum source 709. The vacuum source 709 may apply suction to the fluid collection assembly 700 via the fluid storage container 707. The suction force may be applied directly via the vacuum source 709. For example, the outlet of the conduit 728 may be disposed within the vacuum source 709. An additional conduit 728 may extend from the vacuum source 709 to a point outside of the fluid collection assembly 700, such as to the fluid storage container 707. In such examples, the vacuum source 709 may be disposed between the fluid collection assembly 700 and the fluid storage container 707.

The fluid collection assembly 700 may be similar or identical to any of the fluid collection assemblies disclosed herein in one or more aspects. The fluid collection assembly 700 may be shaped and sized to be positioned adjacent to a female urethral opening or receive a penis.

The fluid storage container 707 is sized and shaped to retain a fluid. The fluid storage container 707 may include a bag (e.g., drainage bag), a bottle or cup (e.g., collection jar), or any other enclosed container for storing bodily fluid(s) such as urine. In some examples, the conduit 728 may extend from the fluid collection assembly 700 and attach to the fluid storage container 707 at a first point. An additional conduit 728 may attach to the fluid storage container 707 at a second point thereon and may extend and attach to the vacuum source 709. A vacuum (e.g., suction) may be drawn through fluid collection assembly 700 via the fluid storage container 707. Fluid, such as urine, may be drained from the fluid collection assembly 700 using the vacuum source 709.

The vacuum source 709 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 709 may provide a vacuum or suction to remove fluid from the fluid collection assembly 700. In some examples, the vacuum source 709 may be powered by one or more of a power cord (e.g., connected to a power socket), one or more batteries, or even manual power (e.g., a hand operated vacuum pump). In some examples, the vacuum source 709 may be sized and shaped to fit outside of, on, or within the fluid collection assembly 700. For example, the vacuum source 709 may include one or more miniaturized pumps or one or more micro pumps. The vacuum sources 709 disclosed herein may include one or more of a switch, a button, a plug, a remote, or any other device suitable to activate the vacuum source 709.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or +2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising:
    a fluid impermeable barrier defining a chamber, at least one opening, and at least one fluid outlet;
    at least one porous material disposed in the chamber;
    at least one inflation device including at least one bladder and at least one valve, the at least one bladder including one or more walls defining at least one interior region, the at least one valve configured to selectively permit at least one inflation fluid to flow into and out of the at least one interior region to switch the at least one bladder between a first state and at least a second state, wherein an amount of the at least one inflation fluid present in the at least one interior region is greater when the at least one bladder is in the second state than when the at least one bladder is in the first state; and
    a conduit disposed in the fluid outlet, wherein the conduit is separate from the at least one inflation device.

2. The fluid collection assembly of claim 1, wherein at least a portion of the at least one inflation device is attached to at least a portion of at least one outer surface of the fluid impermeable barrier.

3. The fluid collection assembly of claim 1, wherein the at least one bladder and the fluid impermeable barrier are integrally formed.

4. The fluid collection assembly of claim 1, wherein at least a portion of the at least one inflation device is positioned between the fluid impermeable barrier and the at least one porous material.

5. The fluid collection assembly of claim 1, wherein the at least one porous material includes at least one fluid permeable membrane and at least one fluid permeable support.

6. The fluid collection assembly of claim 5, wherein at least a portion of the at least one inflation device is positioned between the at least one permeable membrane and the at least one fluid permeable support.

7. The fluid collection assembly of claim 1, wherein the at least one bladder includes a plurality of bladders.

8. The fluid collection assembly of claim 7, further comprising at least one passageway extending between at least two of the plurality of inflation elements.

9. The fluid collection assembly of claim 1, wherein the at least one valve includes a luer valve.

10. The fluid collection assembly of claim 1, wherein the at least one interior region includes substantially none of the at least one inflation fluid therein when the at least one bladder is in the first state.

11. The fluid collection assembly of claim 1, wherein the fluid collection assembly exhibits a first cross-sectional shape when the at least one inflation element is in the first state and a second cross-sectional shape when the at least one bladder is in the second state, wherein the first shape is different than the second shape, the first cross-sectional shape and the second cross-sectional shape measured perpendicular to a longitudinal axis of the fluid collection assembly.

12. The fluid collection assembly of claim 1, wherein the at least one opening is configured to be positioned adjacent to a female urethral opening.

13. A system comprising:
a fluid collection assembly including:
    a fluid impermeable barrier defining a chamber, at least one opening, and at least one fluid outlet;
    at least one porous material disposed in the chamber; and
    at least one inflation device including at least one bladder and at least one valve, the at least one bladder including one or more walls defining at least one interior region, the at least one valve configured to selectively permit at least one inflation fluid to flow into and out of the at least one interior region to switch the at least one bladder between a first state and at least a second state, wherein an amount of the at least one inflation fluid present in the at least one interior region is greater when the at least one bladder is in the second state than when the at least one bladder is in the first state;
a fluid storage container;
a vacuum source; and
one or more conduits operably coupling the at least one fluid outlet of the fluid collection assembly, the fluid storage container, and the vacuum source together.

* * * * *